(12) United States Patent
Martin

(10) Patent No.: US 9,610,070 B2
(45) Date of Patent: Apr. 4, 2017

(54) CLOSURE DEVICE

(75) Inventor: Christopher Martin, Galway (IE)

(73) Assignee: Vivasure Medical Limited, Galway (IE)

(*) Notice: Subject to any disclaimer, the term of this patent is extended or adjusted under 35 U.S.C. 154(b) by 869 days.

(21) Appl. No.: 12/139,926

(22) Filed: Jun. 16, 2008

(65) Prior Publication Data
US 2009/0018574 A1 Jan. 15, 2009

Related U.S. Application Data

(60) Provisional application No. 60/944,168, filed on Jun. 15, 2007.

(51) Int. Cl.
*A61B 17/08* (2006.01)
*A61B 17/00* (2006.01)
*A61B 17/04* (2006.01)

(52) U.S. Cl.
CPC ...... *A61B 17/0057* (2013.01); *A61B 17/0469* (2013.01)

(58) Field of Classification Search
CPC ............ A61B 17/0469; A61B 17/0057; A61B 2017/00575; A61B 2017/00615; A61B 2017/00623; A61B 2017/00628; A61B 2017/00663
USPC ................ 606/108, 139–147, 151, 157, 158, 606/213–221, 232; 623/23.72
See application file for complete search history.

(56) References Cited

U.S. PATENT DOCUMENTS

| | | |
|---|---|---|
| 321,721 A | 7/1885 | Hassan |
| 2,001,638 A | 5/1935 | Elof Tornsjo |
| 2,560,162 A | 7/1951 | Ferguson |
| 2,778,254 A | 1/1957 | Carapellotti |
| 3,874,388 A | 4/1975 | King et al. |
| 4,299,230 A | 11/1981 | Kubota |
| 4,583,540 A | 4/1986 | Malmin |
| 4,650,472 A | 3/1987 | Bates |

(Continued)

FOREIGN PATENT DOCUMENTS

| | | |
|---|---|---|
| DE | 102010048908 A1 | 4/2012 |
| EP | 0761250 A1 | 3/1997 |

(Continued)

OTHER PUBLICATIONS

European Patent Office Partial Supplementary Search Report. Application No. 12784868.7, Jan. 12, 2015, 5 pages.

(Continued)

*Primary Examiner* — Julian W Woo
*Assistant Examiner* — Shaun L David
(74) *Attorney, Agent, or Firm* — Choate, Hall & Stewart LLP; William R. Haulbrook; Alexander D. Augst

(57) ABSTRACT

An interventional medical closure device comprises a first engagement element for engagement with an external surface of a vessel on a first side of an opening through the vessel wall and a second engagement element for engagement with an external surface on a second side of the opening. A closure element extends from the first engagement element, into the vessel, and to the second engagement element to assist in closure of the opening. The device may include a foot element to engage the internal surface of the vessel on both sides of the opening. The foot element may provide a guide with a pathway for the closure element.

39 Claims, 32 Drawing Sheets

(56) References Cited

U.S. PATENT DOCUMENTS

| | | |
|---|---|---|
| 4,705,040 A | 11/1987 | Mueller et al. |
| 4,744,364 A | 5/1988 | Kensey |
| 4,852,568 A | 8/1989 | Kensey |
| 4,890,612 A | 1/1990 | Kensey |
| 4,896,668 A | 1/1990 | Popoff et al. |
| 5,021,059 A | 6/1991 | Kensey et al. |
| 5,037,433 A | 8/1991 | Wilk et al. |
| 5,053,046 A | 10/1991 | Janese |
| 5,085,661 A | 2/1992 | Moss |
| 5,127,412 A | 7/1992 | Cosmetto et al. |
| 5,171,258 A | 12/1992 | Bales et al. |
| 5,192,301 A | 3/1993 | Kamiya et al. |
| 5,269,804 A | 12/1993 | Bales et al. |
| 5,282,827 A | 2/1994 | Kensey et al. |
| 5,330,488 A | 7/1994 | Goldrath |
| 5,336,231 A | 8/1994 | Adair |
| 5,342,393 A | 8/1994 | Stack |
| 5,350,399 A | 9/1994 | Erlebacher et al. |
| 5,366,480 A | 11/1994 | Corriveau et al. |
| 5,391,182 A | 2/1995 | Chin |
| 5,431,639 A | 7/1995 | Shaw |
| 5,462,560 A | 10/1995 | Stevens |
| 5,470,337 A | 11/1995 | Moss |
| 5,501,691 A | 3/1996 | Goldrath |
| 5,501,700 A | 3/1996 | Hirata |
| 5,507,755 A | 4/1996 | Gresl et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,593,422 A | 1/1997 | Muijs Van de Moer et al. |
| 5,601,557 A | 2/1997 | Hayhurst |
| 5,601,571 A | 2/1997 | Moss |
| 5,620,461 A | 4/1997 | Muijs Van De Moer et al. |
| 5,653,716 A | 8/1997 | Malo et al. |
| 5,662,681 A | 9/1997 | Nash |
| 5,665,096 A | 9/1997 | Yoon |
| 5,676,689 A | 10/1997 | Kensey et al. |
| 5,690,674 A | 11/1997 | Diaz |
| 5,700,273 A | 12/1997 | Buelna et al. |
| 5,700,277 A | 12/1997 | Nash et al. |
| 5,707,393 A | 1/1998 | Kensey |
| 5,722,981 A | 3/1998 | Stevens |
| 5,755,727 A | 5/1998 | Kontos |
| 5,782,861 A | 7/1998 | Cragg et al. |
| 5,797,939 A | 8/1998 | Yoon |
| 5,814,065 A | 9/1998 | Diaz |
| 5,817,074 A | 10/1998 | Racz |
| 5,827,281 A | 10/1998 | Levin |
| 5,860,990 A | 1/1999 | Nobles |
| 5,861,003 A | 1/1999 | Latson et al. |
| 5,868,762 A | 2/1999 | Cragg et al. |
| 5,916,236 A | 6/1999 | Muijs Van de Moer et al. |
| 5,935,147 A | 8/1999 | Kensey et al. |
| 5,941,899 A | 8/1999 | Granger et al. |
| 5,954,732 A | 9/1999 | Hart et al. |
| 5,997,515 A | 12/1999 | de la Torre et al. |
| 6,007,563 A | 12/1999 | Nash |
| 6,033,427 A | 3/2000 | Lee |
| 6,056,768 A | 5/2000 | Cates et al. |
| 6,080,183 A | 6/2000 | Tsugita et al. |
| 6,126,675 A | 10/2000 | Shchervinsky |
| 6,136,010 A | 10/2000 | Modesitt |
| 6,179,863 B1 | 1/2001 | Kensey |
| 6,190,400 B1 | 2/2001 | Van De Moer et al. |
| 6,200,328 B1 | 3/2001 | Cragg et al. |
| 6,206,895 B1 | 3/2001 | Levinson |
| 6,241,768 B1 | 6/2001 | Agarwal et al. |
| 6,245,080 B1 | 6/2001 | Levinson |
| 6,296,658 B1 | 10/2001 | Gershony |
| 6,319,263 B1 | 11/2001 | Levinson |
| 6,350,274 B1 | 2/2002 | Li |
| 6,383,208 B1 | 5/2002 | Sancoff et al. |
| 6,395,015 B1 | 5/2002 | Borst et al. |
| 6,398,796 B2 | 6/2002 | Levinson |
| 6,425,911 B1 | 7/2002 | Akerfeldt et al. |
| 6,461,364 B1 | 10/2002 | Ginn |
| 6,485,481 B1 | 11/2002 | Pfeiffer |
| 6,500,184 B1 | 12/2002 | Chan et al. |
| 6,508,828 B1 | 1/2003 | Akerfeldt |
| 6,596,012 B2 | 7/2003 | Akerfeldt et al. |
| 6,596,014 B2 | 7/2003 | Levinson et al. |
| 6,638,286 B1 | 10/2003 | Burbank et al. |
| 6,669,707 B1 | 12/2003 | Swanstrom et al. |
| 6,702,835 B2 * | 3/2004 | Ginn .................. 606/215 |
| 6,730,112 B2 | 5/2004 | Levinson |
| 6,764,500 B1 | 7/2004 | Muijs Van De Moer et al. |
| 6,770,070 B1 | 8/2004 | Balbierz |
| 6,779,701 B2 | 8/2004 | Bailly et al. |
| 6,786,915 B2 * | 9/2004 | Akerfeldt et al. .......... 606/232 |
| 6,860,895 B1 | 3/2005 | Akerfeldt |
| 6,890,342 B2 | 5/2005 | Zhu |
| 6,932,824 B1 | 8/2005 | Roop |
| 6,939,363 B2 | 9/2005 | Akerfeldt |
| 6,942,674 B2 | 9/2005 | Belef |
| 6,949,107 B2 | 9/2005 | Mcguckin |
| 6,949,114 B2 | 9/2005 | Milo |
| 6,964,668 B2 | 11/2005 | Modesitt |
| 6,969,397 B2 | 11/2005 | Ginn |
| 6,984,219 B2 | 1/2006 | Ashby |
| 6,989,022 B2 | 1/2006 | Nowakowski |
| 6,997,940 B2 | 2/2006 | Bonutti |
| 7,001,398 B2 | 2/2006 | Carley |
| 7,001,400 B1 | 2/2006 | Modesitt |
| 7,008,440 B2 | 3/2006 | Sing |
| 7,008,441 B2 | 3/2006 | Zucker |
| 7,008,442 B2 | 3/2006 | Brightbill |
| 7,094,248 B2 | 8/2006 | Bachinski et al. |
| 7,169,168 B2 | 1/2007 | Muijs Van De Moer et al. |
| 7,326,221 B2 | 2/2008 | Sakamoto et al. |
| 7,462,188 B2 * | 12/2008 | McIntosh .................. 606/213 |
| 7,534,248 B2 * | 5/2009 | Mikkaichi et al. .......... 606/144 |
| 7,569,063 B2 | 8/2009 | Bailly et al. |
| 7,662,161 B2 | 2/2010 | Briganti et al. |
| 7,678,133 B2 | 3/2010 | Modesitt |
| 7,753,935 B2 | 7/2010 | Brett et al. |
| 7,846,180 B2 * | 12/2010 | Cerier .................... 606/232 |
| 7,918,868 B2 | 4/2011 | Marshall et al. |
| 7,998,169 B2 | 8/2011 | Modesitt |
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |
| 8,083,767 B2 | 12/2011 | Modesitt |
| 8,137,380 B2 | 3/2012 | Green et al. |
| 8,177,795 B2 | 5/2012 | Niese et al. |
| 8,241,325 B2 | 8/2012 | Modesitt |
| 8,267,942 B2 * | 9/2012 | Szabo et al. ................ 606/139 |
| 8,361,092 B1 | 1/2013 | Asfora |
| 8,597,324 B2 | 12/2013 | Briganti et al. |
| 8,652,166 B2 | 2/2014 | Åkerfeldt |
| 8,821,507 B2 | 9/2014 | Axelson, Jr. et al. |
| 8,906,050 B2 | 12/2014 | Brett et al. |
| 9,060,751 B2 | 6/2015 | Martin et al. |
| 2001/0044631 A1 | 11/2001 | Akin et al. |
| 2002/0019648 A1 | 2/2002 | Akerfeldt et al. |
| 2002/0019649 A1 | 2/2002 | Sikora |
| 2002/0055767 A1 | 5/2002 | Forde et al. |
| 2002/0107506 A1 | 8/2002 | McGuckin et al. |
| 2002/0169377 A1 | 11/2002 | Khairkhahan et al. |
| 2002/0177864 A1 | 11/2002 | Camrud |
| 2003/0050665 A1 | 3/2003 | Ginn |
| 2003/0060846 A1 | 3/2003 | Egnelov et al. |
| 2003/0078598 A1 | 4/2003 | Ginn |
| 2003/0093093 A1 | 5/2003 | Modesitt et al. |
| 2003/0120305 A1 | 6/2003 | Jud et al. |
| 2003/0144695 A1 | 7/2003 | McGuckin et al. |
| 2003/0216756 A1 * | 11/2003 | Klein et al. .................. 606/144 |
| 2004/0082906 A1 | 4/2004 | Tallarida et al. |
| 2004/0092964 A1 | 5/2004 | Modesitt et al. |
| 2004/0092969 A1 | 5/2004 | Kumar |
| 2004/0093025 A1 | 5/2004 | Egnelov |
| 2004/0098044 A1 | 5/2004 | Van de Moer et al. |
| 2004/0133238 A1 | 7/2004 | Cerier |

(56) References Cited

U.S. PATENT DOCUMENTS

| | | |
|---|---|---|
| 2004/0176798 A1 | 9/2004 | Epstein |
| 2004/0243122 A1 | 12/2004 | Auth et al. |
| 2005/0021055 A1 | 1/2005 | Toubia et al. |
| 2005/0033326 A1 | 2/2005 | Briganti et al. |
| 2005/0070957 A1 | 3/2005 | Das |
| 2005/0149065 A1 | 7/2005 | Modesitt |
| 2005/0209613 A1 | 9/2005 | Roop et al. |
| 2005/0251201 A1 | 11/2005 | Roue et al. |
| 2005/0267520 A1 | 12/2005 | Modesitt |
| 2005/0273135 A1 | 12/2005 | Chanduszko et al. |
| 2005/0288706 A1 | 12/2005 | Widomski et al. |
| 2006/0100665 A1 | 5/2006 | Von Oepen et al. |
| 2006/0106418 A1 | 5/2006 | Seibold et al. |
| 2006/0142784 A1 | 6/2006 | Kontos |
| 2006/0142797 A1 | 6/2006 | Egnelov |
| 2006/0265008 A1 | 11/2006 | Maruyama et al. |
| 2007/0112385 A1 | 5/2007 | Conlon |
| 2007/0135826 A1 | 6/2007 | Zaver et al. |
| 2007/0179509 A1 | 8/2007 | Nagata et al. |
| 2007/0179527 A1 | 8/2007 | Eskuri et al. |
| 2007/0197858 A1 | 8/2007 | Goldfarb et al. |
| 2007/0255313 A1 | 11/2007 | Modesitt |
| 2007/0282351 A1 | 12/2007 | Harada et al. |
| 2007/0282373 A1 | 12/2007 | Ashby et al. |
| 2008/0228204 A1 | 9/2008 | Hamilton et al. |
| 2008/0243148 A1 | 10/2008 | Mikkaichi et al. |
| 2008/0312646 A9 | 12/2008 | Auth et al. |
| 2009/0048559 A1 | 2/2009 | Grathwohl |
| 2009/0088723 A1 | 4/2009 | Khosravi et al. |
| 2009/0112257 A1 | 4/2009 | Preinitz et al. |
| 2009/0143621 A1 | 6/2009 | Stupak |
| 2009/0312786 A1 | 12/2009 | Trask et al. |
| 2010/0022823 A1 | 1/2010 | Goldfarb et al. |
| 2010/0094425 A1 | 4/2010 | Bentley et al. |
| 2010/0125296 A1 | 5/2010 | Modesitt |
| 2010/0152772 A1 | 6/2010 | Brett et al. |
| 2010/0228184 A1 | 9/2010 | Mavani et al. |
| 2011/0077667 A1 | 3/2011 | Singhatat et al. |
| 2011/0082495 A1 | 4/2011 | Ruiz |
| 2011/0087270 A1 | 4/2011 | Penner et al. |
| 2011/0224728 A1 | 9/2011 | Martin et al. |
| 2012/0089166 A1 | 4/2012 | Modesitt |
| 2012/0296275 A1 | 11/2012 | Martin et al. |
| 2013/0274795 A1 | 10/2013 | Grant et al. |
| 2014/0018846 A1 | 1/2014 | Grant et al. |
| 2014/0018847 A1 | 1/2014 | Grant et al. |
| 2014/0345109 A1 | 11/2014 | Grant et al. |

FOREIGN PATENT DOCUMENTS

| | | |
|---|---|---|
| EP | 0894475 A1 | 2/1999 |
| EP | 2260770 A2 | 12/2010 |
| WO | WO-94/08513 A1 | 4/1994 |
| WO | WO-00/33744 A1 | 6/2000 |
| WO | WO-02/102236 A2 | 12/2002 |
| WO | WO-2006/117766 A2 | 11/2006 |
| WO | WO-2007/011353 A2 | 1/2007 |
| WO | WO-2008/042229 A2 | 4/2008 |
| WO | WO-2008/152617 A2 | 12/2008 |
| WO | WO-2010/027693 A2 | 3/2010 |
| WO | WO-2010/123821 A1 | 10/2010 |
| WO | WO-2011/080588 A2 | 7/2011 |
| WO | WO-2012/090069 A2 | 7/2012 |
| WO | WO-2012/156819 A2 | 11/2012 |
| WO | WO-2013/128292 A2 | 9/2013 |
| WO | WO-2014/141209 A1 | 9/2014 |

OTHER PUBLICATIONS

Extended European Search Report, Application No. EP 11852355.4, Sep. 28, 2015, 7 pages.
Grant et al., Hales' 1733 Haemastaticks, Anesthesiology, 112:1:65 (2010).
Hales, Stephen, Statical Essays, vol. 2 (1773).
International Preliminary Report on Patentability, PCT/IB2010/003461, Jul. 12, 2012, 10 pages.
International Preliminary Report on Patentability, PCT/IE2006/000043, Oct. 30, 2007, 10 pages.
International Search Report, PCT/IB2010/003461, Oct. 11, 2011, 6 pages.
International Search Report, PCT/IB2011/003295, Jun. 29, 2012, 4 pages.
International Search Report, PCT/IB2012/001101, Jan. 30, 2013, 3 pages.
International Search Report, PCT/IB2013/000839, Jan. 14, 2014, 6 pages.
International Search Report, PCT/IB2014/059848, Jul. 7, 2014, 5 pages.
Written Opinion, PCT/IB2010/003461, Oct. 11, 2011, 9 pages.
Written Opinion, PCT/IB2011/003295, Jun. 29, 2012, 5 pages.
Written Opinion, PCT/IB2012/001101, Jan. 30, 2013, 5 pages.
Written Opinion, PCT/IB2013/000839, Jan. 14, 2014, 11 pages.
Written Opinion, PCT/IB2014/059848, Jul. 7, 2014, 8 pages.
Written Opinion, PCT/IE2006/000043, Oct. 29, 2007, 9 pages.

* cited by examiner

CLOSURE DEVICE

This application claims benefit under 35 U.S.C. §119(e) of Provisional Application No. 60/944,168 filed Jun. 15, 2007, the entire disclosure of which is incorporated herein by reference.

INTRODUCTION

This invention relates to an interventional medical closure device, and to a method of performing an interventional procedure to effect closure of openings in membranes, septums, vessel or cavity walls etc. In particular the invention relates to a device which will allow closure of openings within vessel walls, without the aid of direct vision. A vessel meaning any fluid (being liquid or gas) carrying cavity, conduit or space contained by a wall or membrane.

SUMMARY OF THE INVENTION

According to an embodiment of the invention there is provided an interventional medical closure device comprising a closure element configured to extend through a vessel wall to assist in closure of an opening through the vessel wall.

In one embodiment of the invention, the closure element is configured to extend through a first part of a vessel wall on a first side of an opening through the vessel wall into an internal lumen of the vessel, and to extend through a second part of the vessel wall on a second side of the opening out of the internal lumen. The closure element may comprise a suture member.

In one case the device comprises at least one engagement element for engagement with an external surface of a vessel. The engagement element may be configured to engage an external surface of an arterial wall. The device may comprise a first engagement element for engagement with an external surface of a vessel on a first side of an opening through the vessel wall, and a second engagement element for engagement with an external surface of the vessel on a second side of the opening.

According to one aspect the invention provides an interventional medical closure device comprising:
- a first engagement element for engagement with an external surface of a vessel on a first side of an opening through a vessel wall;
- a second engagement element for engagement with an external surface on a second side of the opening; and
- a closure element for extending from the first engagement element, into the vessel, and to the second engagement element to assist in closure of the opening.

The closure element may be extendable through one or both of the engagement elements. The closure element may be coupleable to one or both of the engagement elements.

In one embodiment at least one of the engagement elements has an anterior side and a posterior side, the anterior side having an anterior opening therein, and the posterior side having a posterior opening therein. The openings may be of different dimensions. In one case one of the openings is generally circular and the other opening comprises a slot. The first engagement element may have a generally circular anterior opening and the posterior opening comprises a slot. The second engagement element may have a generally circular posterior opening and the anterior opening comprises a slot.

The engagement element may be movable between a delivery configuration and an engagement configuration. In the engagement configuration, the engagement element may define a substantially flat engagement surface for engagement with an external surface of a vessel. The flat engagement surface acts to distribute the engagement force over a larger surface area to minimise the possibility of trauma to the tissue. The engagement element may comprise a bolster.

In one embodiment the device comprises a foot element. The foot element may be engagable with an internal surface of a vessel to assist in closure of an opening through the vessel wall.

In another embodiment the foot element provides a guide element for guiding passage of the closure element. The guide element may comprise a passageway extending therethrough or open channel, through which the closure element is extendable. The guide/foot element may comprise a substantially curved engagement surface for engagement with an internal surface of a vessel. The engagement surface may be curved in a convex shape. The guide/foot element may have a substantially porous contact surface to minimise the contact surface area with engagement tissue. At least part of the guide/foot element may be biocompatible or biodegradable. Because the guide/foot element is biocompatible, the guide/foot element may remain within the internal lumen after completion of the interventional procedure.

In another case the device comprises a delivery element to deliver the guide element into an internal lumen of a vessel. The guide element may be movable relative to the delivery element between a delivery configuration and an engagement configuration. In the delivery configuration, the guide element may present a low-profile for ease of delivery via a tubular element. The delivery element may be sufficiently stiff to hold the guide element in the deployed configuration, once free of the tubular element. The delivery element may be stiffened by a concentric holding element. The holder element may hold the guide element in a desired location and/or orientation relative to the vessel. The guide element may be detachable from the delivery element to deploy the guide element in an internal lumen of a vessel. The device may comprise a tubular element through which the delivery element and the guide element may be delivered through a vessel wall into a lumen. The tubular element may comprise a procedural sheath or cannula.

In another aspect the invention provides an engagement element for engaging with an external surface of a vessel on one side of an opening through a vessel wall, the engagement element having an anterior side and a posterior side, the anterior side having an anterior opening and the posterior side having a posterior opening. In one case the openings are of different dimensions. One of the openings may be generally circular and the other opening comprises a slot. In one case the engagement element has a generally circular anterior opening and the posterior opening comprises a slot. In another case the engagement element has a generally circular posterior opening and the anterior opening comprises a slot.

In a further aspect the invention provides an interventional medical closure device comprising a foot element which is adapted to engage the internal surface of a vessel on both sides of an opening in the vessel wall. The foot element may provide a tamponade. In one case the foot element is movable between a delivery configuration and an engagement configuration. The foot element may be engageable with an internal surface of a vessel to assist in closure of an opening through the vessel wall. In one case the foot element comprises a profiled engagement surface for engagement with an internal surface of a vessel. The engagement surface may be curved in a convex shape. The foot element may have a substantially porous contact surface. In one case the foot element comprises a guide for guiding a closure element. The guide element may comprise a pathway for a closure element. In one case the pathway comprises a passageway through the guide element. The pathway may comprise an open channel.

In a further aspect the invention provides a method of performing an interventional procedure, the method comprising:
- providing a first engagement element, a second engagement element, and a closure element;
- placing the first engagement element at external surface at a first side of an opening in a vessel wall;
- placing the second engagement element at the external surface at a second side of the opening in the vessel wall; and
- extending the closure element from the first engagement element, into the vessel and to the second engagement element to assist in closure of the opening.

In one case the closure element is extended through a first part of the vessel wall on the first side of the opening into an internal lumen of the vessel, and extended through a second part of the vessel wall on the second side of the opening out of the internal lumen. The method may comprise engaging the external surface of the vessel with at least one of the engagement elements. In one case the external surface of the vessel on the first side of the opening is engaged with the first engagement element, and the external surface of the vessel on the second side of the opening is engaged with the second engagement element. The closure element may be extended through at least one of the engagement elements. In one case the method comprises the step of coupling the closure element to at least one of the engagement elements. In one embodiment the method comprises moving at least one of the engagement elements between a delivery configuration and an engagement configuration. In one embodiment the method comprises providing a foot element and the method comprises engaging the foot element with the internal surface of the vessel on both sides of the opening. The method may comprise delivering the foot element into the internal lumen. In one case the method comprises moving the foot element between a delivery configuration and an engagement configuration. The method may comprise holding the foot element in the engagement configuration. In one embodiment the foot element comprises a guide for the closure member and the method comprises leading the closure member through a pathway in the guide. In one case the foot element is delivered to the vessel through a tubular element.

In another aspect of the invention there is provided a method of performing an interventional procedure, the method comprising the:
- creating an opening through a vessel wall; and
- extending a closure element through the vessel wall to assist in closure of the opening.

In one embodiment of the invention the closure element is extended through a first part of the vessel wall on a first side of the opening into an internal lumen of the vessel, and extended through a second part of the vessel wall on a second side of the opening out of the internal lumen, by operation of attachment to a closure element delivery component. The closure element delivery component may comprise a flexible needle. The closure element delivery component may be rendered flexible by way of the intrinsic hyper-elastic properties of the material, such as nitinol, or by operation of circumferential cuts in a hypotube. The circumferential cuts may be configured such that the closure element delivery component is flexible in a single axis only. In one case, the method comprises engaging the external surface of the vessel with an engagement element. The vessel may comprise an arterial wall. The external surface of the vessel on the first side of the opening may be engaged with a first engagement element, and the external surface of the vessel on the second side of the opening may be engaged with a second engagement element. The closure element may be extended through the engagement elements. The method may comprise coupling the closure element to the engagement element. The method may comprise moving the engagement element between a delivery configuration and an engagement configuration. In the engagement configuration the first and second engagement elements effect a closing of the opening in the vessel.

In another embodiment the method comprises using a guide element to guide passage of the closure element delivery component and closure element. The method may comprise engaging the guide element with an internal surface of the vessel to assist in closure of the opening. The method may comprise delivering the guide element into the internal lumen. The method may comprise moving the guide element between a delivery configuration and a deployed configuration. The method may comprise holding the guide element in the deployed configuration.

In another embodiment the guide element is delivered to the vessel lumen through a tubular element.

BRIEF DESCRIPTION OF THE DRAWINGS

The invention will be more clearly understood from the following description of an embodiment thereof, given by way of example only, with reference to the accompanying drawings, in which.

DETAILED DESCRIPTION

Figure 1:
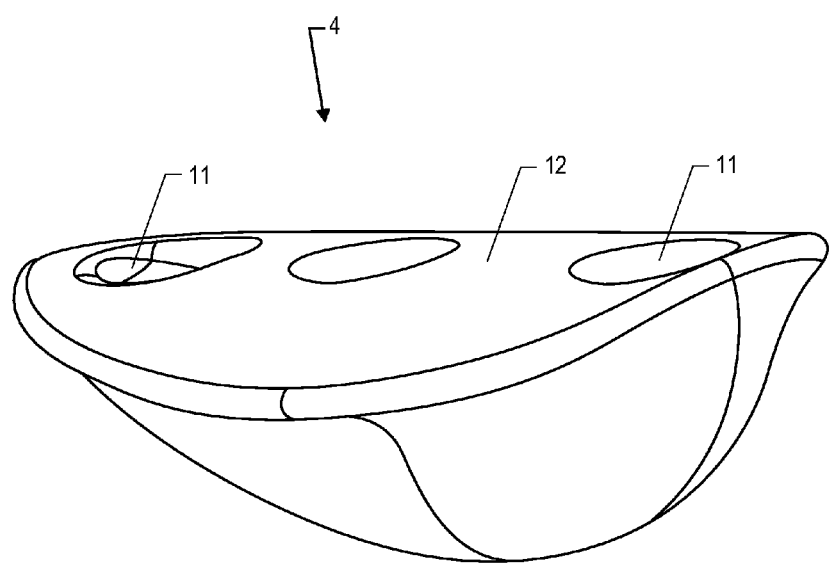
FIG. 1 is an isometric view of a foot or guide element of an interventional medical closure device according to the invention.

Referring to the drawings, there is illustrated an interventional medical closure device according to various embodiments of the present invention. The device comprises a closure element 1, a first engagement element 2, a second engagement element 3, a foot guide element 4, a delivery element 5, and a tubular element 6.

Figure 9:
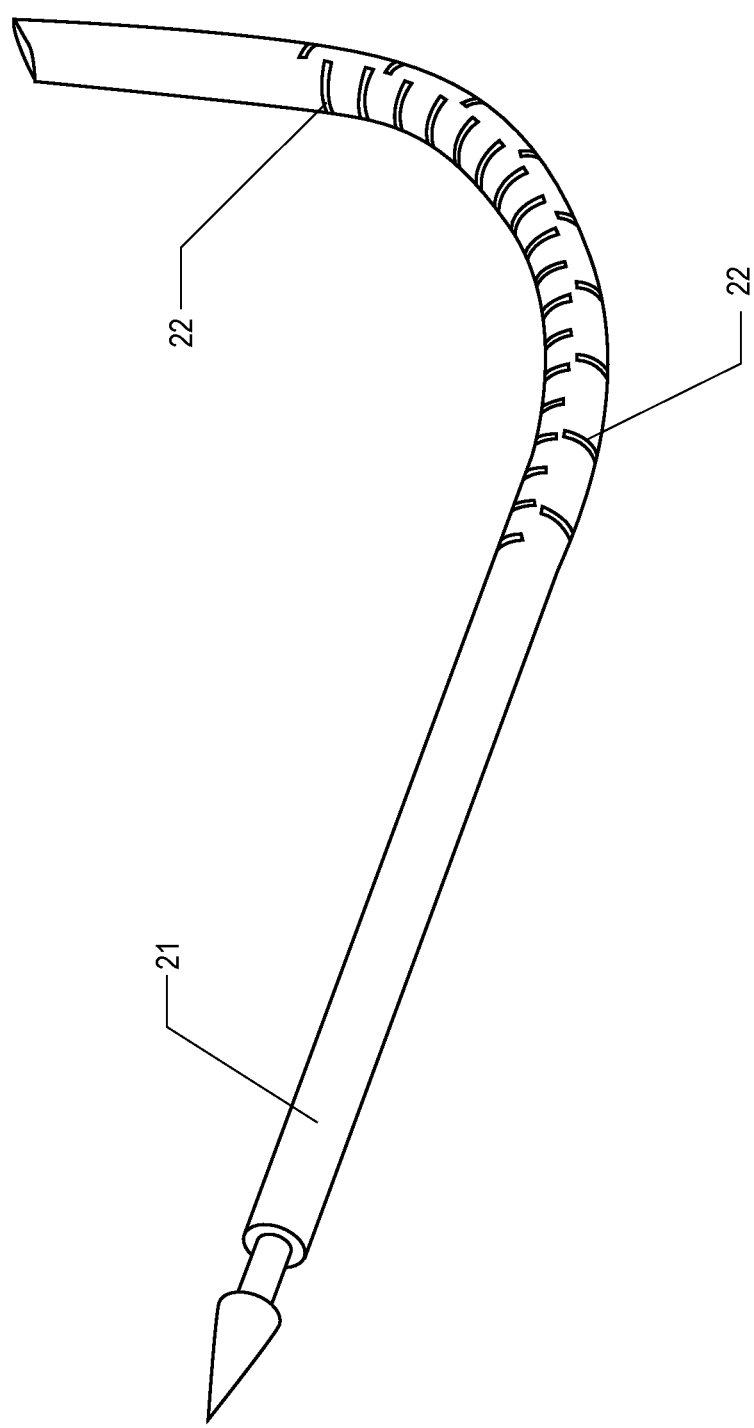
FIG. 9 is an isometric view of a closure element delivery element.

The closure element 1 is provided in this case in the form of a suture. The suture may be braided and may be made from a bioabsorbable material. The closure element, or suture in this case, is attached to a closure element delivery component 16. The closure element delivery component may be a flexible needle, made from a hyper-elastic nitinol material. The closure element delivery component in another embodiment may be a flexible hypotube 21, made flexible by the configuration of a series of circumferential cuts 22. The circumferential cuts 22, may be configured in such a way as to render the needle flexible in one Cartesian-coordinate plane only and more flexible in one direction only. FIG. 9 illustrates the interventional medical closure element which comprises the tubular main body part 21 and the needle at the end of the main body part 21. The main body part 21 is provided in the form of a hypotube in this case. The hypotube 21 has a series of circumferential discontinuities, for example slots 22, in the wall of the hypotube 21. The slots 22 facilitate lateral flexing of the hypotube 21.

The closure element 1 may be extended through a first part of a vessel wall 7 on a first side of an opening 8 through the vessel wall into an internal lumen 9 of the vessel, and extended through a second part of the vessel wall 10 on a second side of the opening 8 out of the internal lumen 9. In this manner the closure element 1 may be employed to assist closure of the opening 8.

In one implementation of the present invention, the vessel wall is an arterial wall.

Each of the engagement elements 2, 3 is provided in this case in the form of a cylindrically shaped bolster. The closure element 1 is extendable through each of the engagement elements 2, 3, and the closure element 1 may be coupled to each engagement element 2, 3. When the closure element 1 has been extended through the engagement elements 2, 3 and is coupled to the engagement elements 2, 3, the first engagement element 2 engages with the external surface of the vessel on the first side of the opening 8, and the second engagement element 3 engages with the external surface of the vessel on the second side of the opening 8 (FIG. 31).

Each engagement element 2, 3 is movable between a delivery configuration and an engagement configuration. In the engagement configuration, each engagement element 2, 3 defines an engagement surface which is profiled to engage against the external surface of the vessel (FIG. 31). The engagement surface may be flat or curved to suit the profile of the vessel surface.

The foot or guide element 4 has a pathway for the closure element 1. In one case the pathway comprises a passageway 11 extending through the element 4. In an alternative embodiment the pathway 11 may comprise of an open channel. The closure element 1 may be extended through the passageway 11. In this manner the guide element 4 guides passage of the closure element 1 from when it enters the internal lumen 9 on the first side of the opening 8 to when it exits the internal lumen 9 on the second side of the opening 8.

Figure 31:
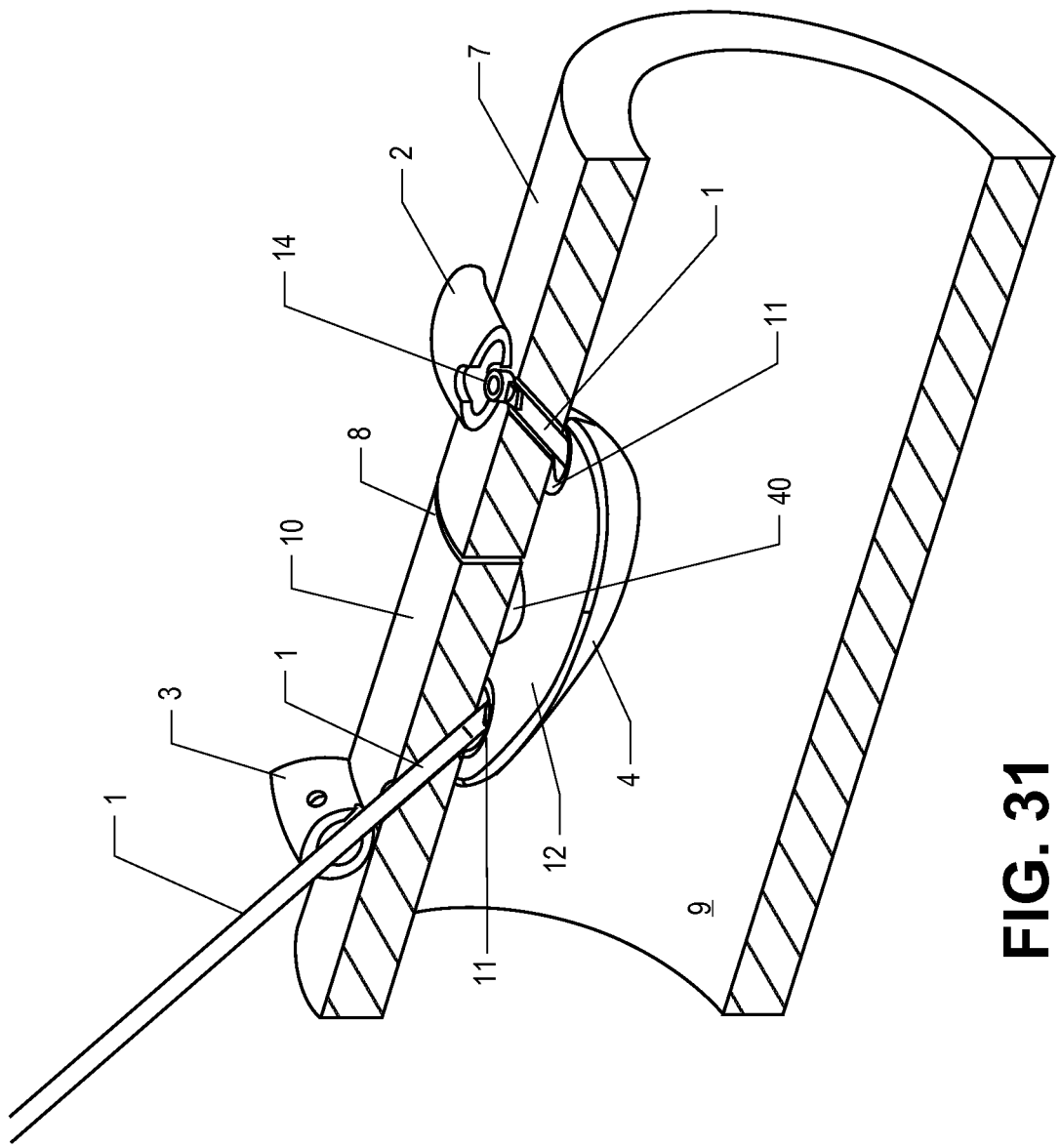
FIG. 31 is a cut-away, isometric view of the closure system in situ.

The guide element 4 also engages the internal surface of the vessel on both sides of the opening 8 (FIG. 31). In this manner the guide element 4 assists in closure of the opening 8.

The upper engagement surface 12 of the guide element 4, which engages with the internal surface of the vessel, is curved in a convex shape (FIG. 2) to mate with the curvature of the internal surface of the vessel.

Figure 12:
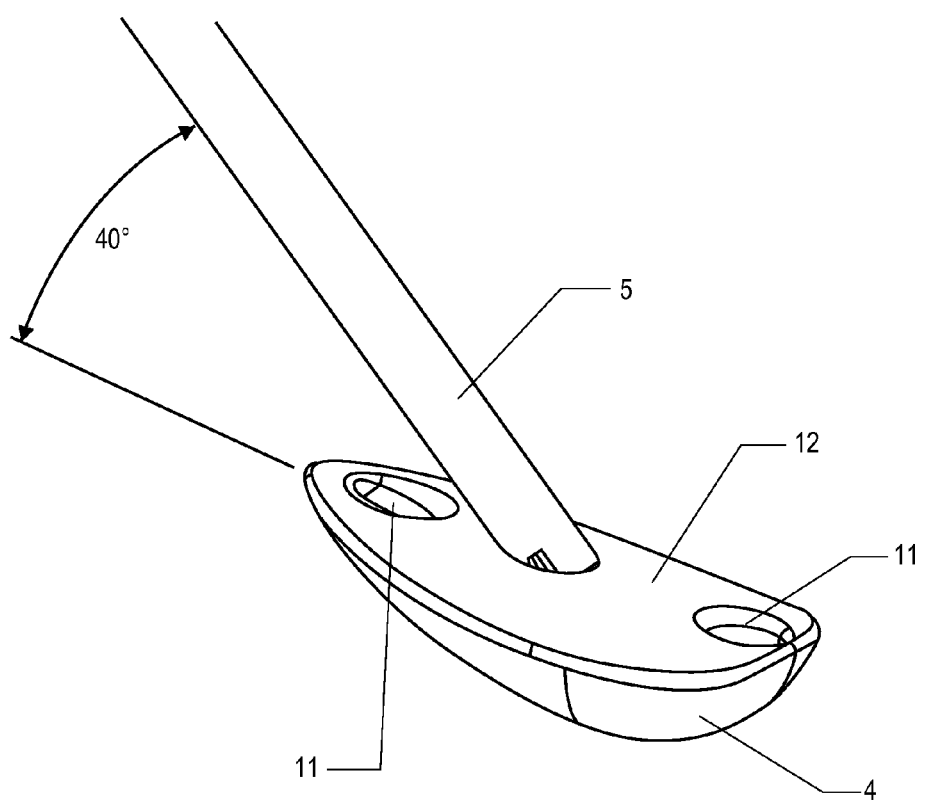
FIG. 12 is an isometric view of the guide element of FIG. 1 and the delivery element of FIG. 9.
Figure 14:
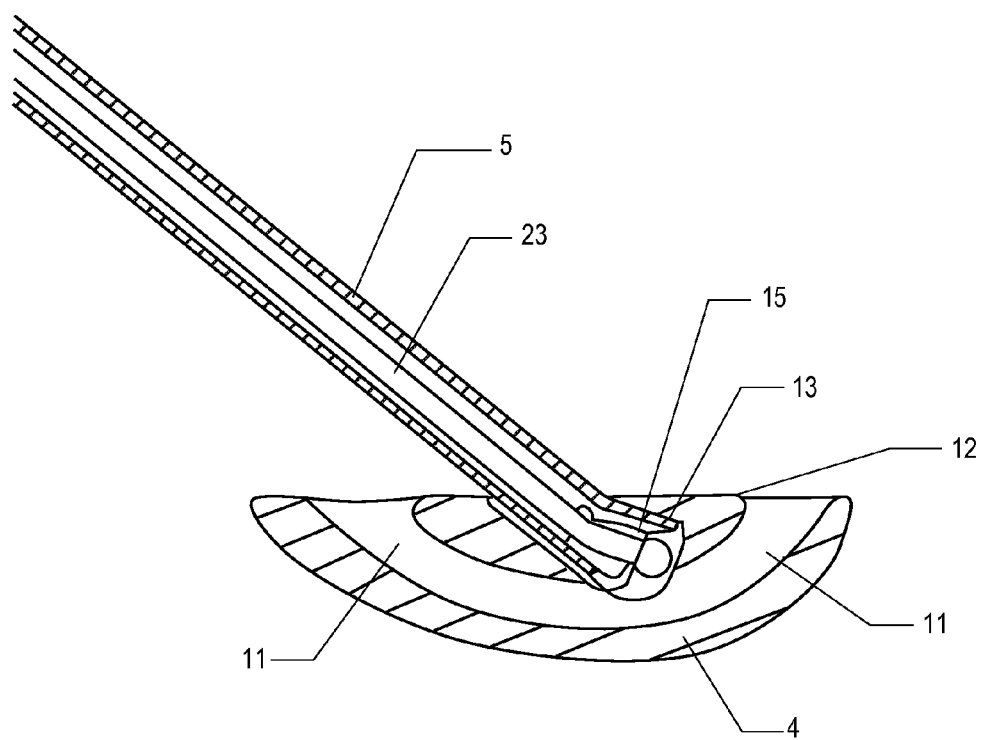
FIGS. 14 and 15 are cross-sectional, side views of the guide element and delivery element.
Figure 15:
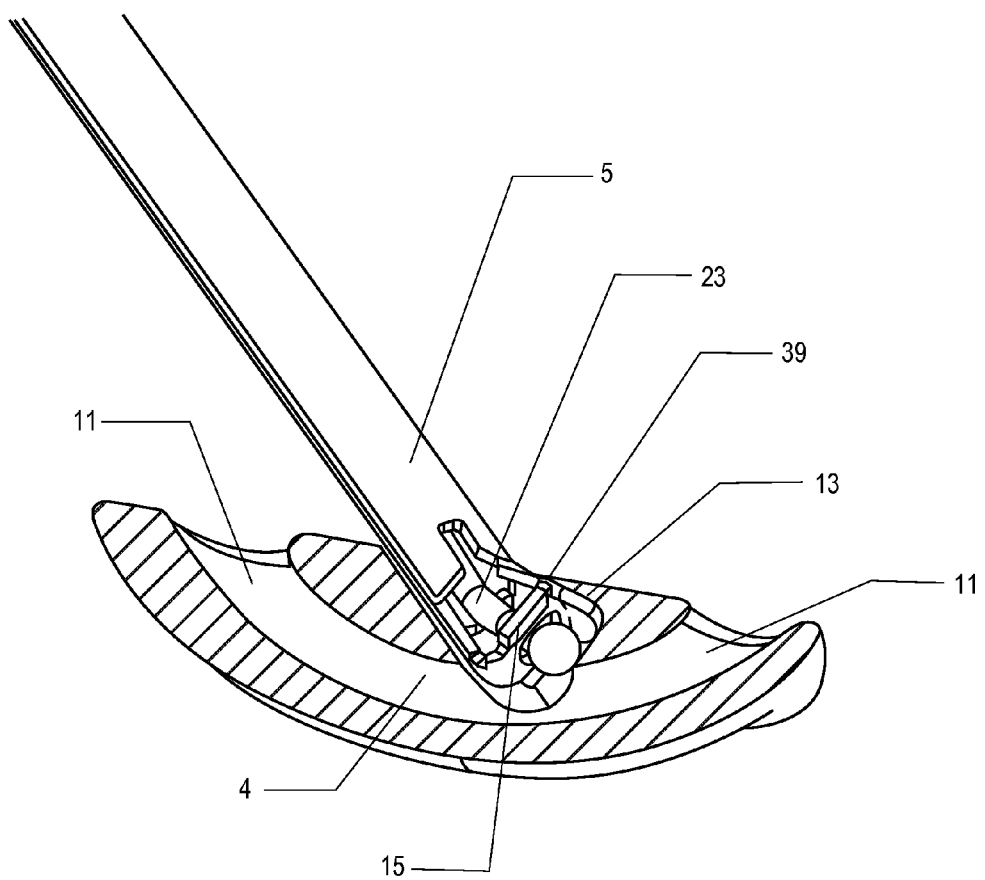

The delivery element 5 may be employed to deliver the guide element 4 into the internal lumen 9. The guide element 4 is movable relative to the delivery element 5 between a delivery configuration (FIG. 10) and a deployed configuration (FIG. 12). The delivery element 5 comprises a holder element 13 supported by a collapsible support element 15 to releasably hold the guide element 4 in the delivery and deployed configurations (FIGS. 14 and 15).

The guide element 4 may be detached from the delivery element 5 to deploy the guide element 4 in the internal lumen 9, by collapsing the support element by application of a tension to the release element 23. The guide element 4 may then remain in the internal lumen 9 after completion of the interventional procedure, as a functional part of the closure system. The guide element 4 may be manufactured from a biodegradable material.

The tubular element 6 is provided in the form of a procedural sheath. The guide element 4 and the delivery element 5 may be delivered through the tubular element 6 to the vessel lumen.

The interventional medical closure device may also comprise a stabiliser element 20 which is engagable with the external surface of the vessel to stabilise the guide element 4 relative to the vessel. The stabiliser element 20 is movable between a tubular delivery configuration inclined at an angle relative to the vessel wall (FIG. 11A), and a flattened deployed configuration parallel to the vessel wall (FIG. 11B).

Figure 11A:
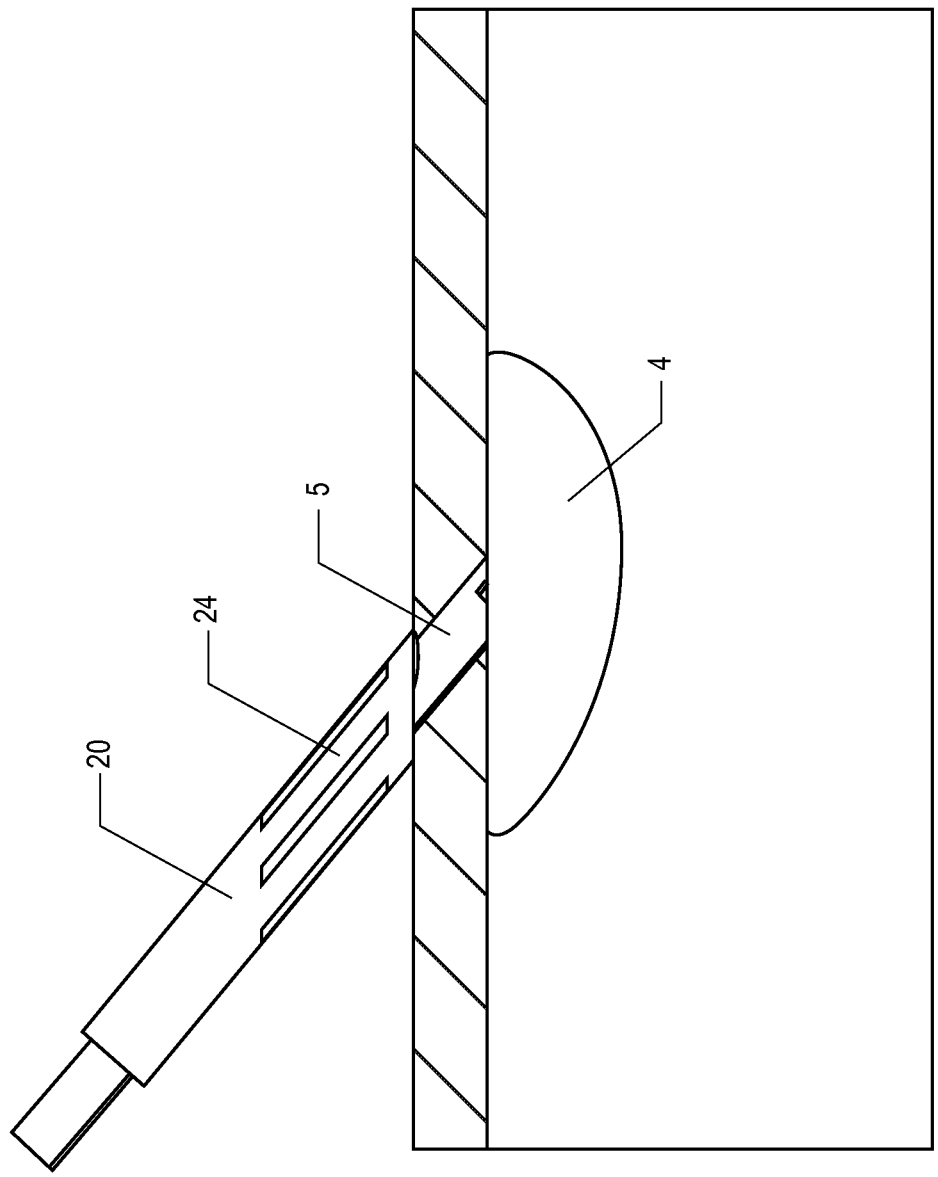
FIG. 11A is a side view of the interventional device showing a clamping element and guide element.
Figure 11B:
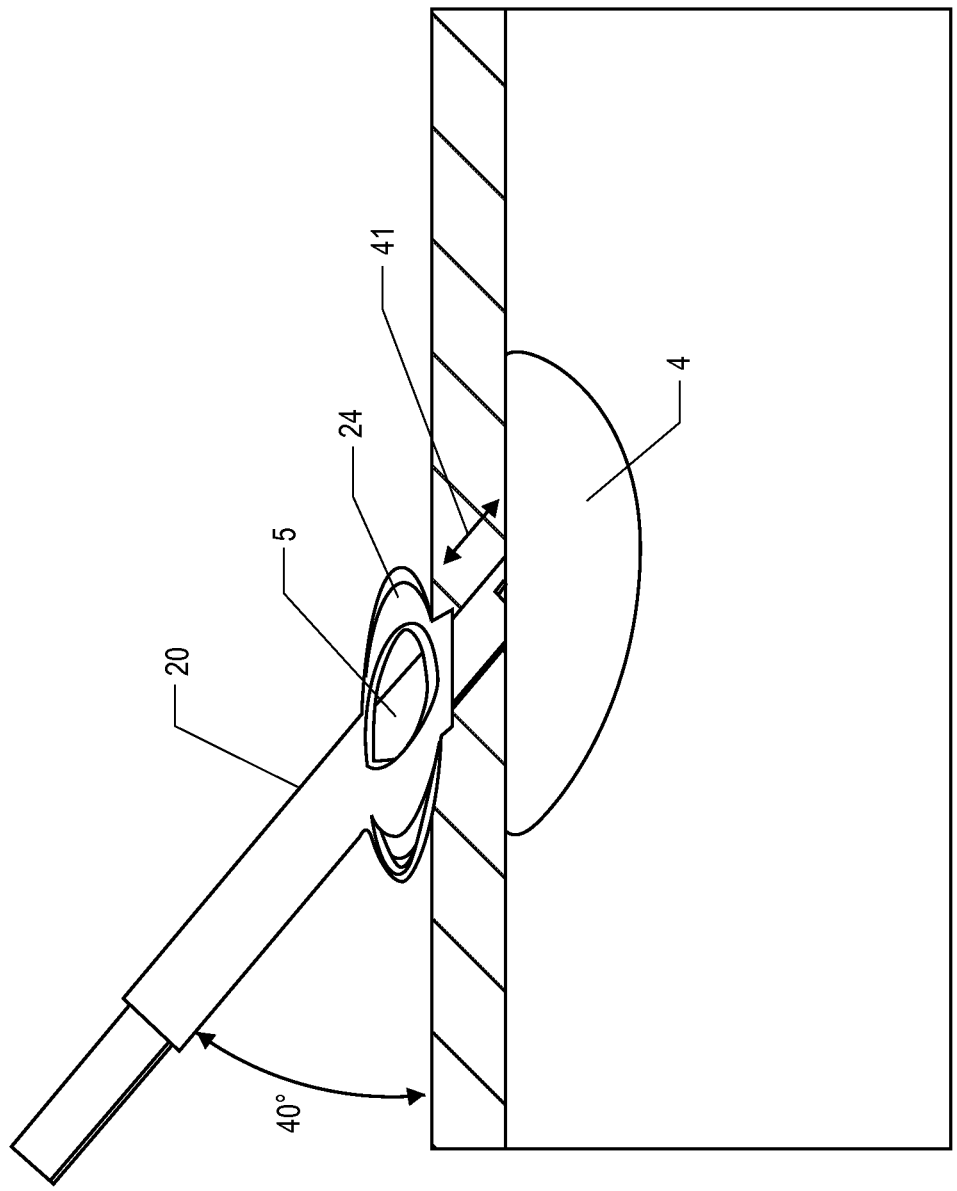
FIG. 11B is a side view of the interventional device showing the clamping element deployed and guide element.

To temporarily secure the guide element 4 in juxtaposition to the opening 8, the clamping element 20 may be employed on the external wall of the vessel (FIGS. 11A and 11B). Deployment of the clamping element 20 is achieved by an axial compressive motion of the clamping element 20, FIG. 11A, to cause the clamp element 24 to balloon outwardly, FIG. 11B. To maintain a clamping action of the guide element 4 to the vessel wall, the clamping element 20 is held fixed to the delivery element 5 at an appropriate off-set 41 proximal to the guide element 4, FIG. 11B.

Figure 10:
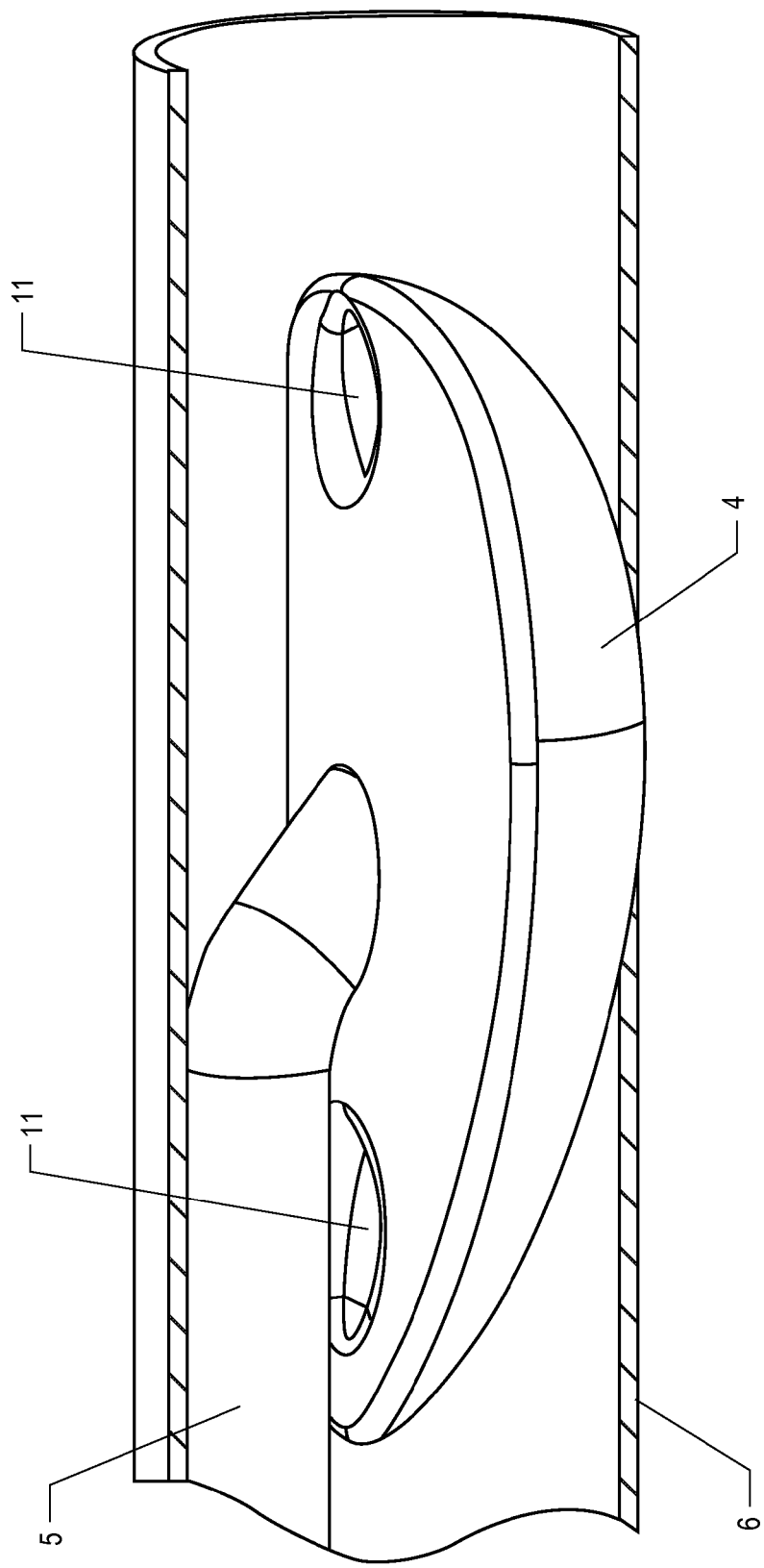
FIG. 10 is an isometric view of the guide element of FIG. 1, a delivery element and a tubular element of the interventional medical closure device according to the invention.

In use, the opening 8 is created through the vessel wall, in one application the anterior wall of an artery. The guide element 4 in the delivery configuration and the delivery element 5 are delivered to the vessel through the tubular element 6 (FIG. 10). The guide element 4, the delivery element 5 and the clamping element 20 are advanced out of the tubular element 6, which is already through the opening 8, into the internal lumen 9. The guide element 4 is moved relative to the delivery element 5 from the delivery configuration to the deployed configuration (FIGS. 12 and 11A). The guide element is temporarily held in position by the clamping element 20, FIG. 11B.

Figure 23:
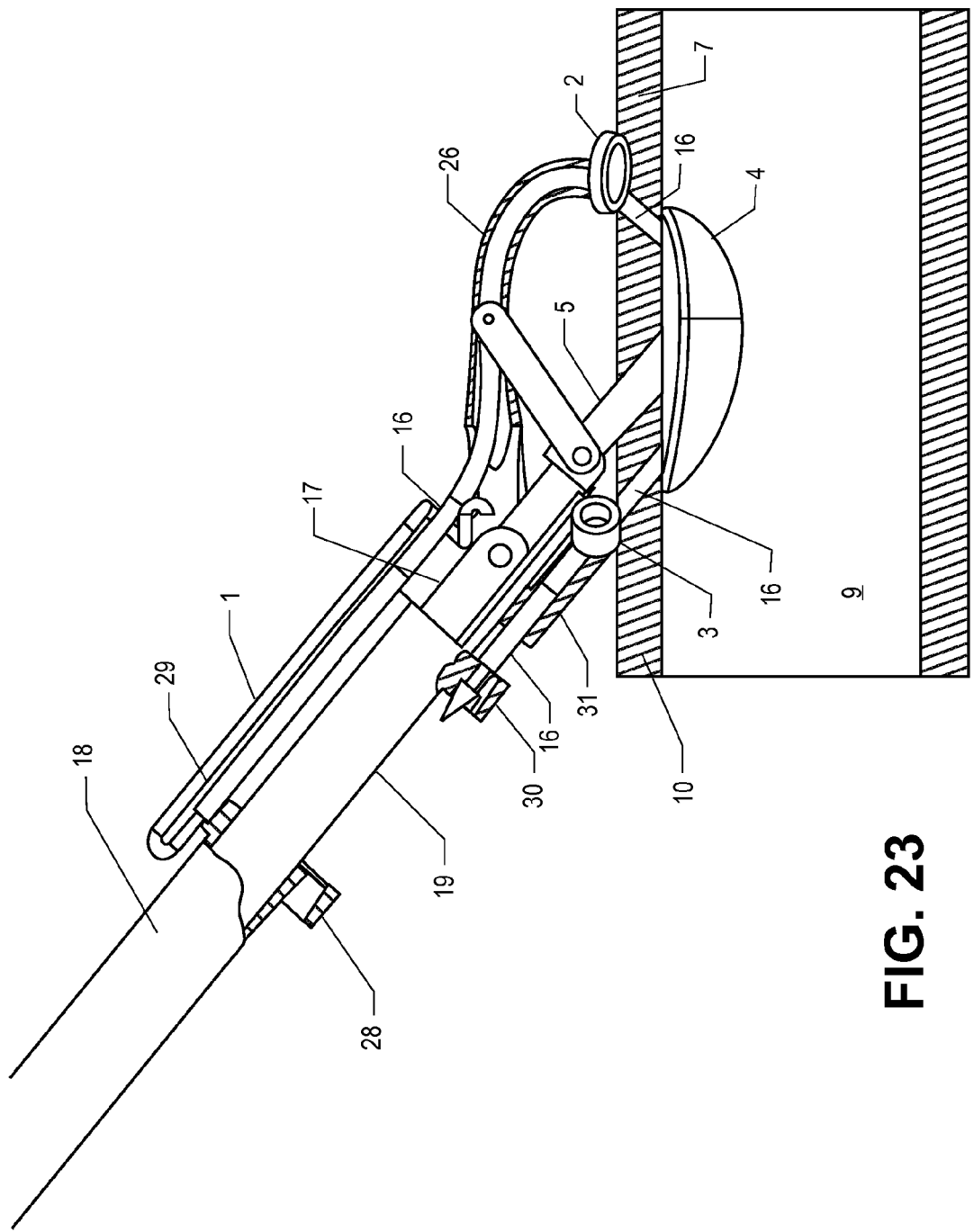
FIG. 23 is a side view of the interventional medical closure device, in use.

The engagement elements 2, 3 are delivered to the external surface of the vessel (FIGS. 16 to 21). The closure element delivery component 16 is extended through the first engagement element 2, through the first part of the vessel wall 7 (FIGS. 20 and 21), through the passageway 11 of the guide element 4, through the second part of the vessel wall 10, and through the second engagement element 3 (FIG. 23).

Figure 28:
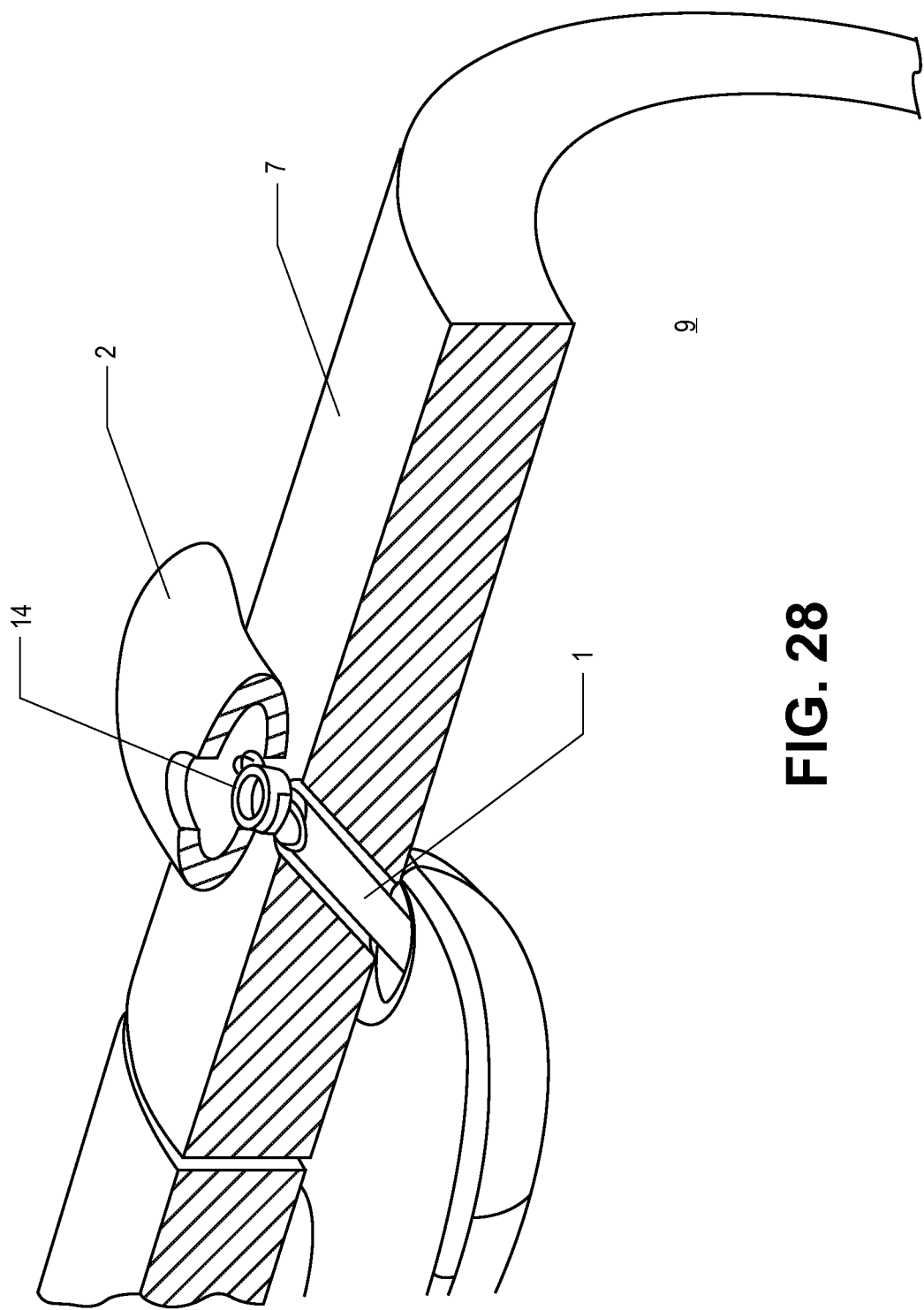
FIG. 28 is a cut-away, isometric view of part of the interventional medical closure device, in situ.

The leading end of the closure element delivery component 16 is drawn proximally away from the second engagement element 3 (FIG. 26) until the proximal end 14 of the closure element 1 engages the first engagement element 2 (FIG. 28). In this manner the closure element 1 is coupled to the first engagement element 2, and the engagement elements 2, 3 are moved from the delivery configuration to the engagement configuration. The guide element 4 is detached from the delivery element 5 and the delivery element 5 is withdrawn from the opening 8.

The guide element 4 remains in the internal lumen 9 engaging the internal surface of the vessel on both sides of the opening 8 with the engagement elements 2 and 3 engaging the external surface of the vessel (FIG. 31). The guide element 4, closure element 1, closure element anchor 14 and engagement elements 2 and 3 may remain as permanent implants or alternatively may bioabsorb/biodegrade, depending on material selection.

The engagement surface of the guide/foot element 4 may be curved in a convex shape. The element 4 may be configured for minimal contact. For example, the element may have a substantially porous contact surface to minimise the contact surface area with engagement tissue and allow nutrient exchange.

The invention relates to a percutaneous arterial closure device. The device of the invention may be employed for percutaneous closure of arteriotomies following endovascular/intraarterial procedures. The target artery may be the common femoral artery.

The procedural sheath 6, which is used to gain intraarterial access, is shown in FIG. 10.

Introduction of the intraarterial-foot 4 is delivered via the procedural sheath 6, as shown in FIG. 10. The intraarterial-foot 4 is attached or anchored to the flexible cylindrical member intraarterial-foot-anchor 5, used to deploy the intraarterial-foot 4 into the artery.

Figure 2:
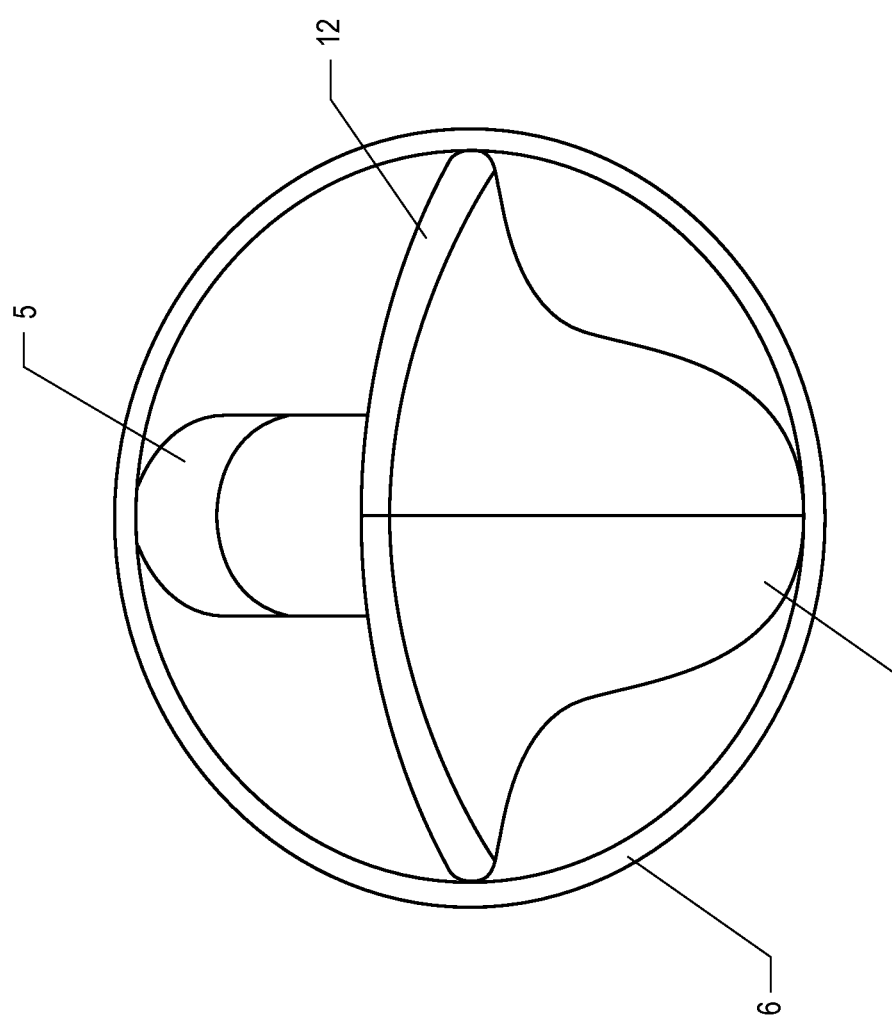
FIG. 2 is an end view of the guide element of FIG. 1 within a tubular element.

The intraarterial-foot 4 is designed to be marginally wider than the internal diameter of the procedural sheath 6 to encourage an elliptical distortion of the sheath, FIG. 2. This is to prevent the leading edge or tip of the foot 4 contacting the procedure sheath 6 during its insertion through the sheath 6 and causing excessive drag or wedging of the intraarterial-foot 4 within the sheath 6. The trailing edge or bottom and sides of the intraarterial-foot 4 and bent intraarterial-foot-anchor 5 contact the procedural sheath 6. FIG. 2 illustrates an end-view of the procedural sheath 6 with the intraarterial-foot 4 in situ, showing the elliptical distortion and contact points during insertion of the intraarterial-foot 4 through the procedural sheath 6.

The intraarterial-foot 4 is advanced through the procedural sheath 6 until it is fully deployed within the artery as shown in FIG. 11A. Once the intraarterial-foot 4 is free of the procedural sheath 6, the intraarterial-foot-anchor 5 actively, by nature of its stiffness, rotates the intraarterial-foot 4 into its final orientation, relative to the intraarterial-foot-anchor 5, for example at 40°, FIG. 12.

The procedural sheath 6 can now be withdrawn from the artery and subcuticular tissue tract, whilst repositioning the intraarterial-foot 4 against the luminal surface of the anterior arterial wall juxtaposition to the arteriotomy, as shown in FIG. 11A. The foot 4 held in this position will form an effective tamponade to control any arterial bleeding.

Figure 3:
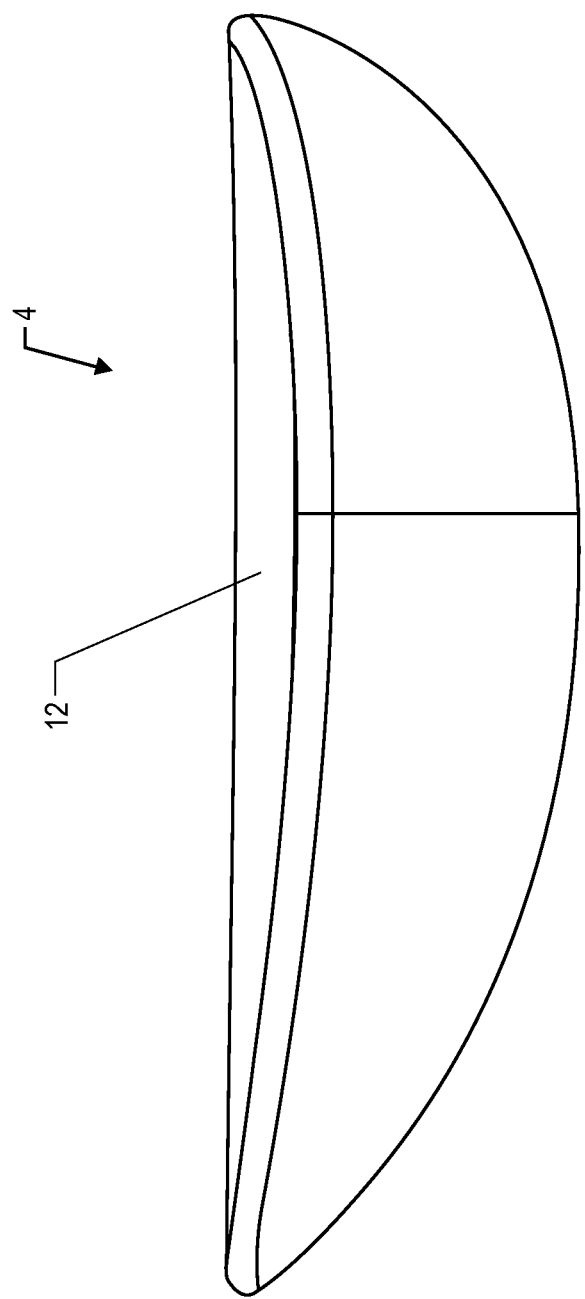
FIG. 3 is a side view of the guide element of FIG. 1.

To ensure the intraarterial-foot 4 is held securely in juxtaposition to the arteriotomy, against the lumen, the extraarterial-clamp 20 is compressed to cause the extraarterial-clamp struts 24 to balloon outwardly, to clamp the intraarterial-foot 4 to the luminal surface of the arterial wall, FIG. 11B. Both the extraarterial-clamp 20 and the intraarterial-foot 4 in this configuration, FIG. 11B, act as a tamponade to control any arterial bleeding. The extraarterial-clamp struts 24 are configured to encourage them to fold out at an angle parallel to the intraarterial-foot 4, for example 40°, FIG. 11B. The intraarterial-foot 4 is profiled and streamlined to minimise haemodynamic effects, FIGS. 1 to 3.

Figure 13:
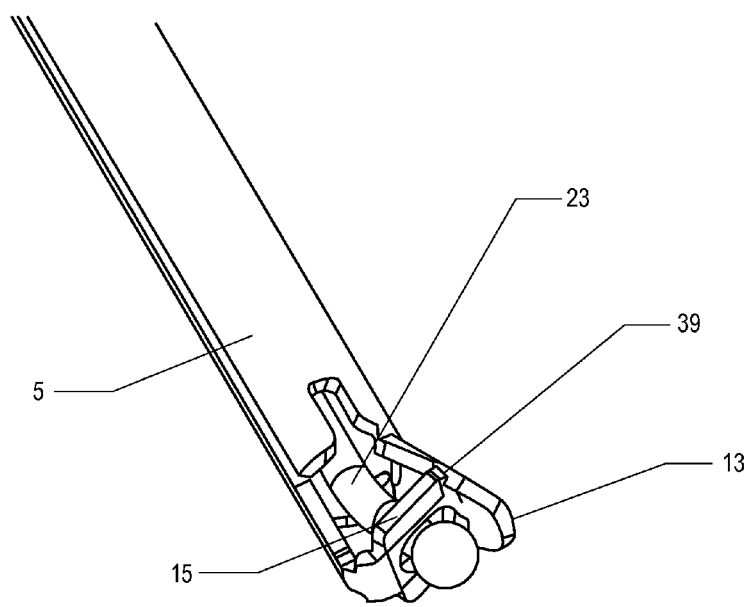
FIG. 13 is an isometric view of the delivery element of FIG. 9.

The intraarterial-foot 4 once located in its intended position in juxtaposition to the arteriotomy is required to be oriented, relative to the arteriotomy and arterial axis. To ensure the correct orientation of the intraarterial-foot 4, the intraarterial-foot-anchor 5 engages with the intraarterial-foot 4, in such a way as to infer rotational stability. This interlock between the intraarterial-foot 4 and the intraarterial-foot-anchor 5 is achieved by a collapsible wedge 13. FIG. 13 illustrates the collapsible wedge 13 of the intraarterial-foot-anchor 5 and FIGS. 14 and 15 illustrates the intraarterial-foot-anchor 5 engaged with the intraarterial-foot 4.

Figure 30:
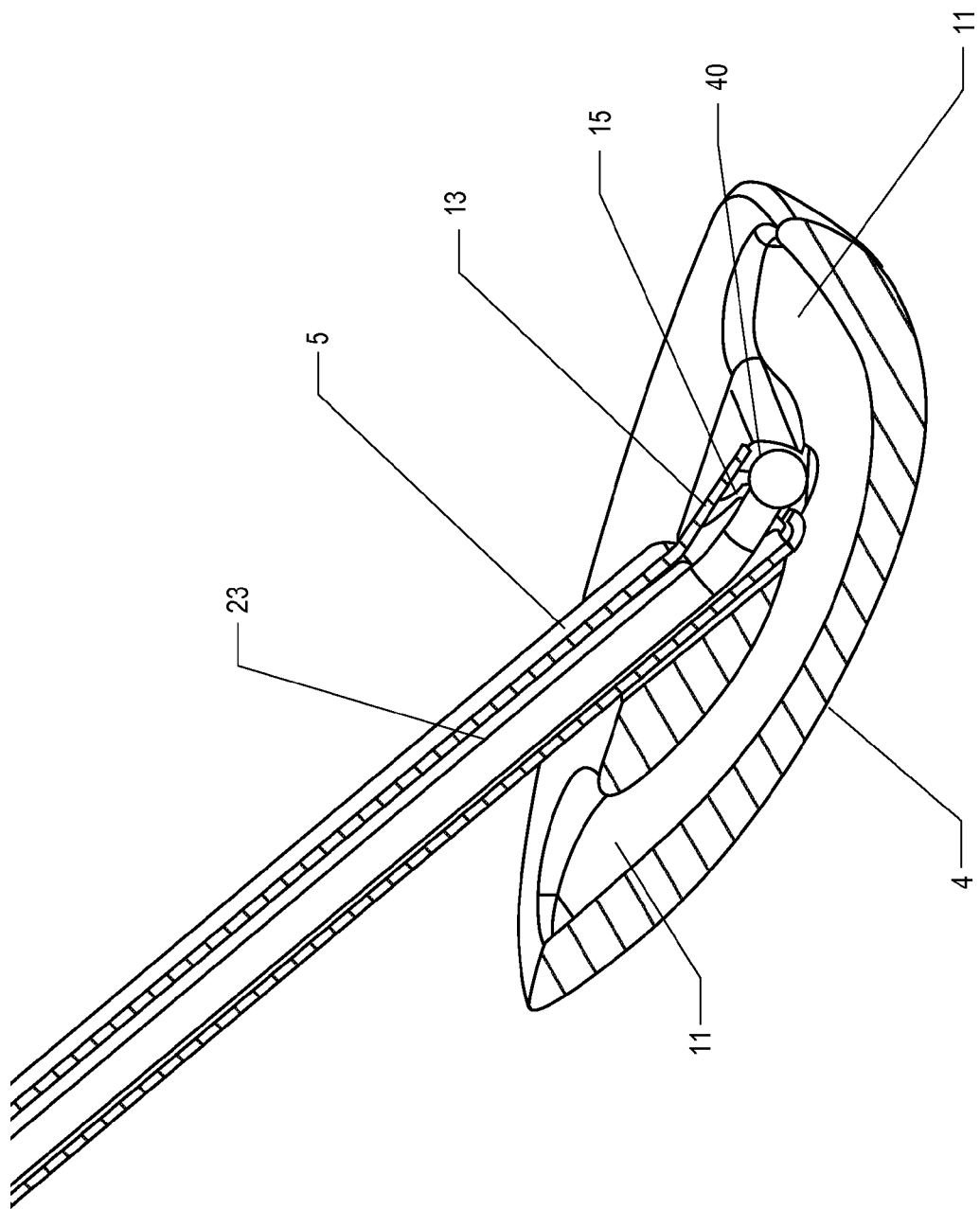
FIG. 30 is a cut-away, isometric views of the delivery element and guide element.

The wedge 13 is collapsible in order to release the intraarterial-foot 4 when appropriate. Collapsing of the wedge 13 is achieved by applying tension to the release wire 23, causing the collapsible support 15 to collapse, as shown in FIG. 30. The hyper-elastic nature of the material used for the intraarterial-foot-anchor 5 (nitinol) causes the wedge 13 to return to its original cylindrical configuration, when unsupported, as shown in FIG. 30. The intraarterial-foot-anchor 5 is then free to be withdrawn from the intraarterial-foot 4. The wedge/cylindrical shape of the interlock also ensure the intraarterial-foot-anchor 5 is atraumatic to the arterial wall and surrounding tissues during withdrawal.

The intraarterial-foot 4 once correctly positioned in juxtaposition to the arteriotomy may serve two functions, namely: 1) to control the arterial bleeding and form an integral part of the closure system, and 2) act as a needle guide to guide a flexible needle intraarterially from one side of the arteriotomy to the other. In this way the delivery system of the arterial closure device becomes part of the implantable closure system itself.

In an alternative embodiment the needle guide channel may be an open channel and rely on a pre-curved needle or flexible shuttle to guide the needle and suture from one side of the arteriotomy to the other.

The intraarterial-foot-anchor 5 may also serve two functions: 1) to facilitate the delivery of the intraarterial-foot 4 into the lumen of the artery and anchoring the intraarterial-foot 4 in its correct position; and 2) the intraarterial-footanchor 5 also acts as a percutaneous guide for the suture 1 and bolster 2, 3 delivery system, with or without the procedural sheath in situ.

Figure 16:
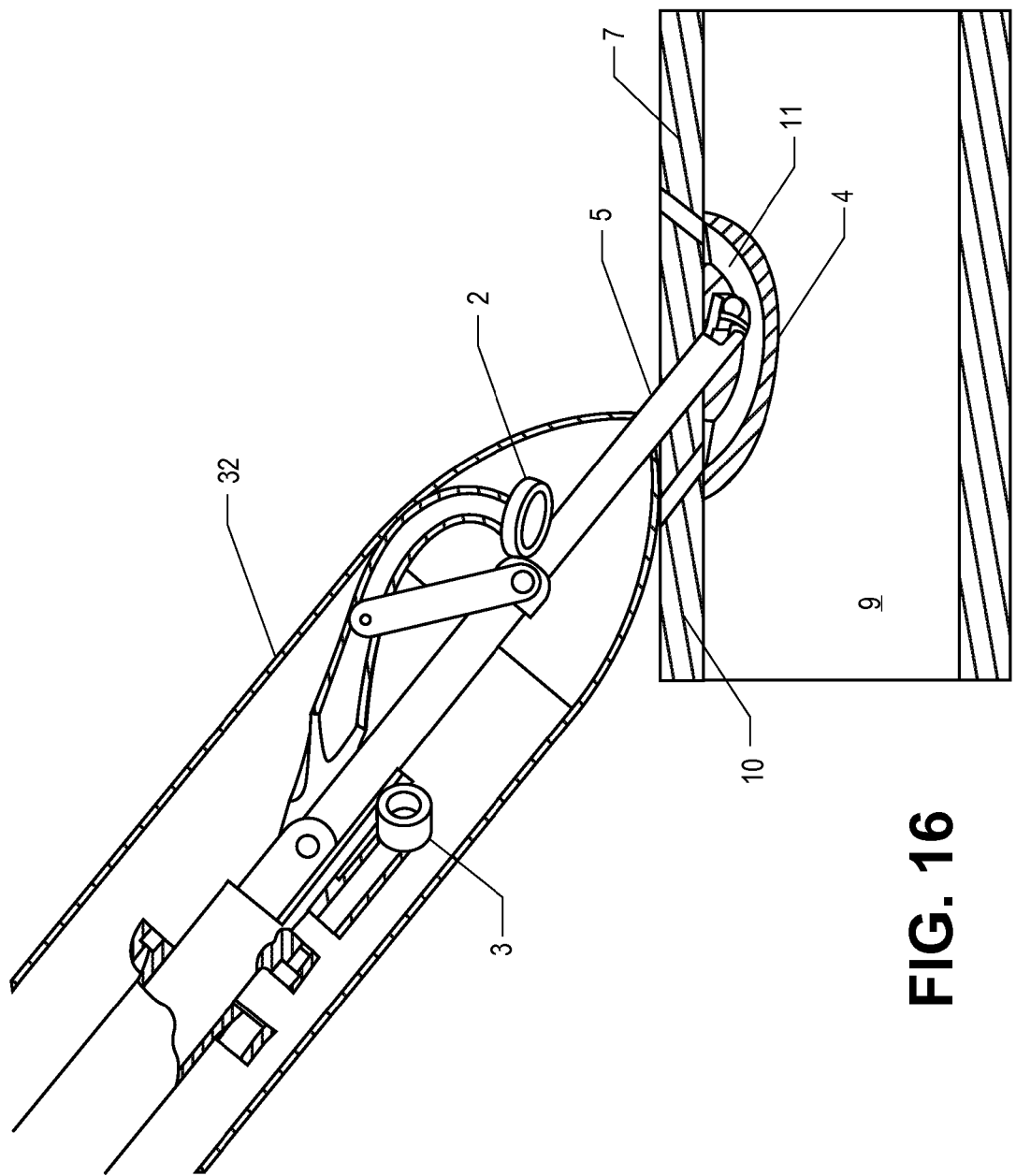
FIGS. 16 to 21 are cross-sectional, side views of the interventional closure device, in various states of use.

Once the intraarterial-foot 4 is correctly positioned and the procedural sheath 6 has been removed from the arteriotomy, the suture 1 and bolster 2, 3 delivery system is percutaneously guided down the intraarterial-foot-anchor 5 to its pre-deployment position, adjacent to the arterial wall. To aid the suture 1 and bolster 2, 3 delivery system's tracking through the skin and subcuticular tissue and minimise any further dilation or trauma to these tissues, they may be housed in a splitable-sheath 32 which is smoothly transitioned to the shaft diameter of the intraarterial-foot-anchor 5. The splitable-sheath 32 housing the suture 1 and bolster 2, 3 delivery system is shown in FIG. 16, in its final subcuticular position adjacent the arteriotomy. FIG. 16 illustrates the splitable-sheath 32 housing the suture 1 and bolster 2, 3 delivery system, in position adjacent the arteriotomy, prior to splitting. Alternatively, the suture 1 and bolster 2, 3 delivery system may be delivered percutaneously via the procedural sheath, which has been withdrawn from the arteriotomy but remaining extraarterial within the subcuticular tissue tract.

Figure 17:
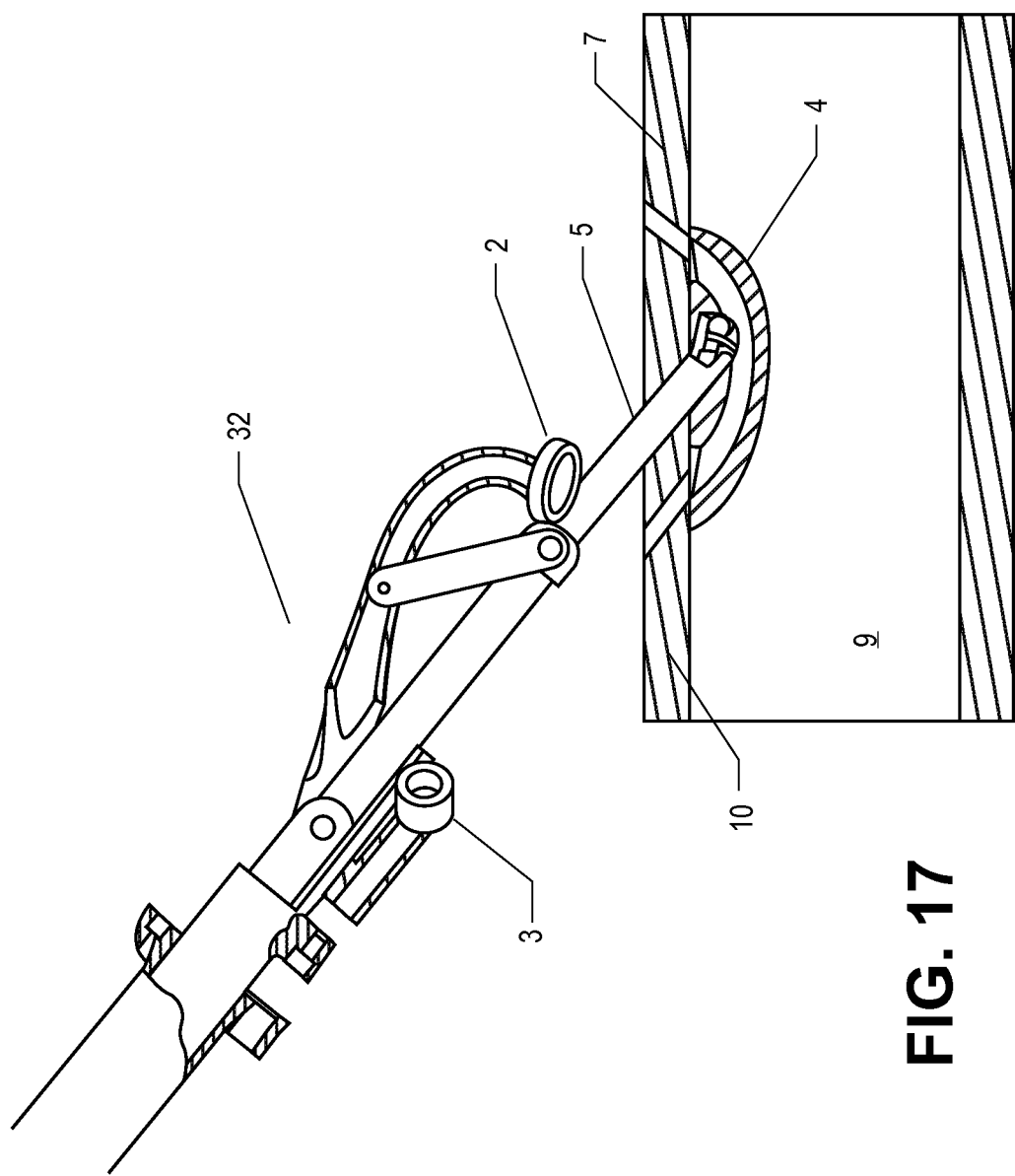
Figure 18:
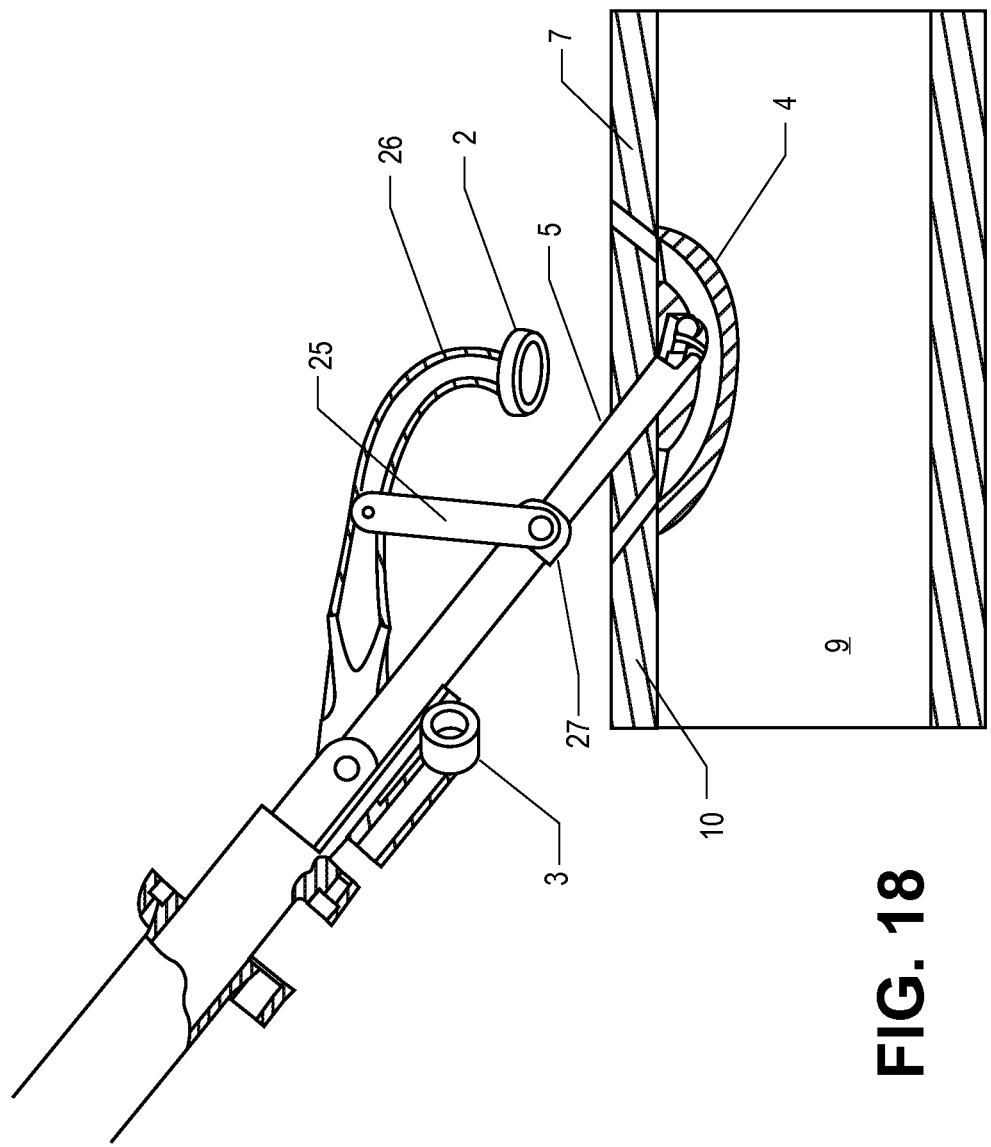

Once properly positioned adjacent to the arteriotomy, the splitable-sheath 32 is removed to expose the suture 1 and bolster 2, 3 delivery system. FIG. 17 illustrates the suture 1 and bolster 2, 3 delivery system with the split-sheath 32 removed. The suture 1 and bolster 2, 3 delivery system is then activated, in one embodiment, in the following sequence:

The needle-guide-link-actuator 27 is retracted concentrically about the intraarterial-foot-anchor 5, to cause the needle-guide-link 25 to extend the needle-guide 26. FIG. 18 illustrates actuation of the needle-guide-link-actuator 27 to extend the needle-guide 26.

Figure 19:
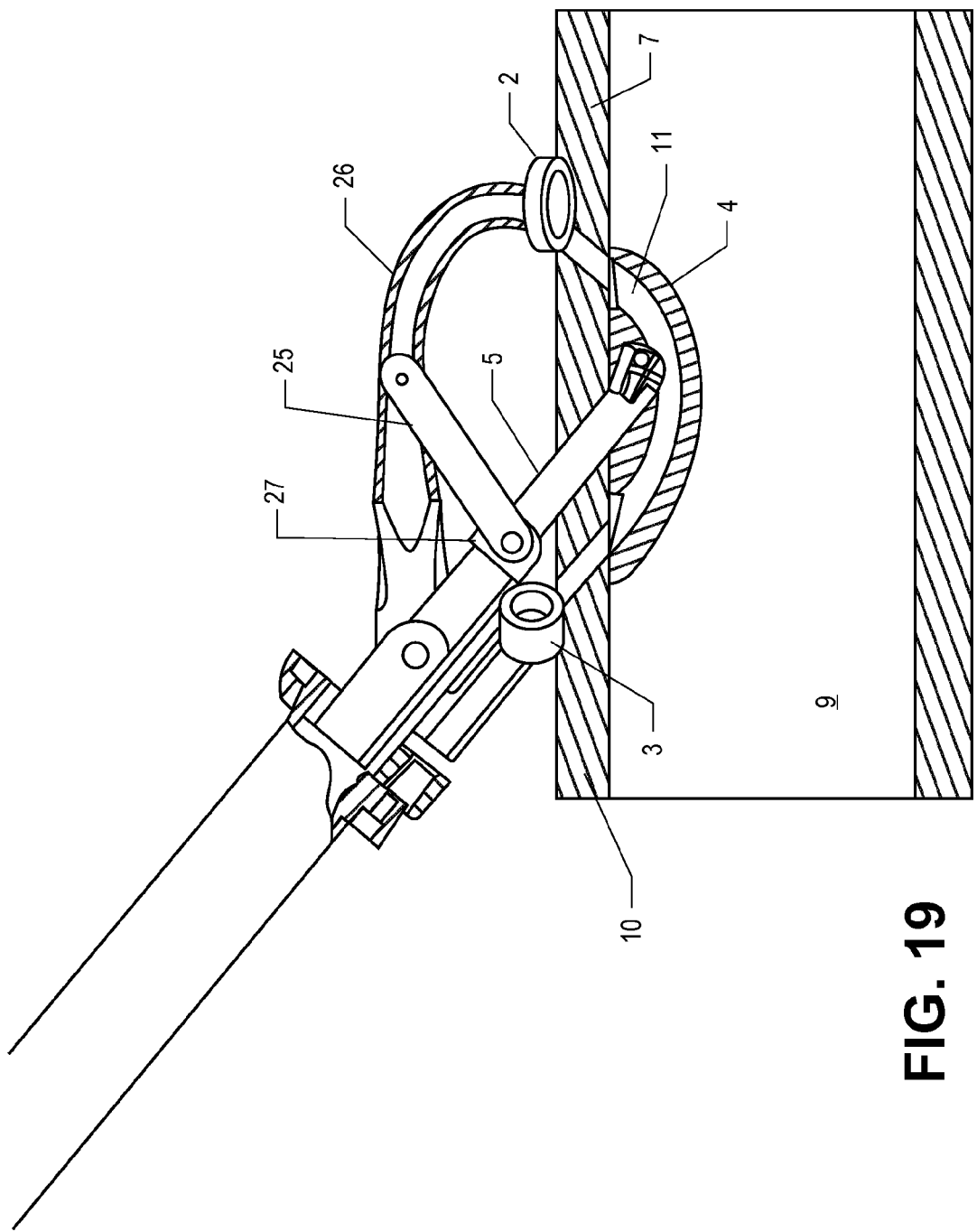
Figure 20:
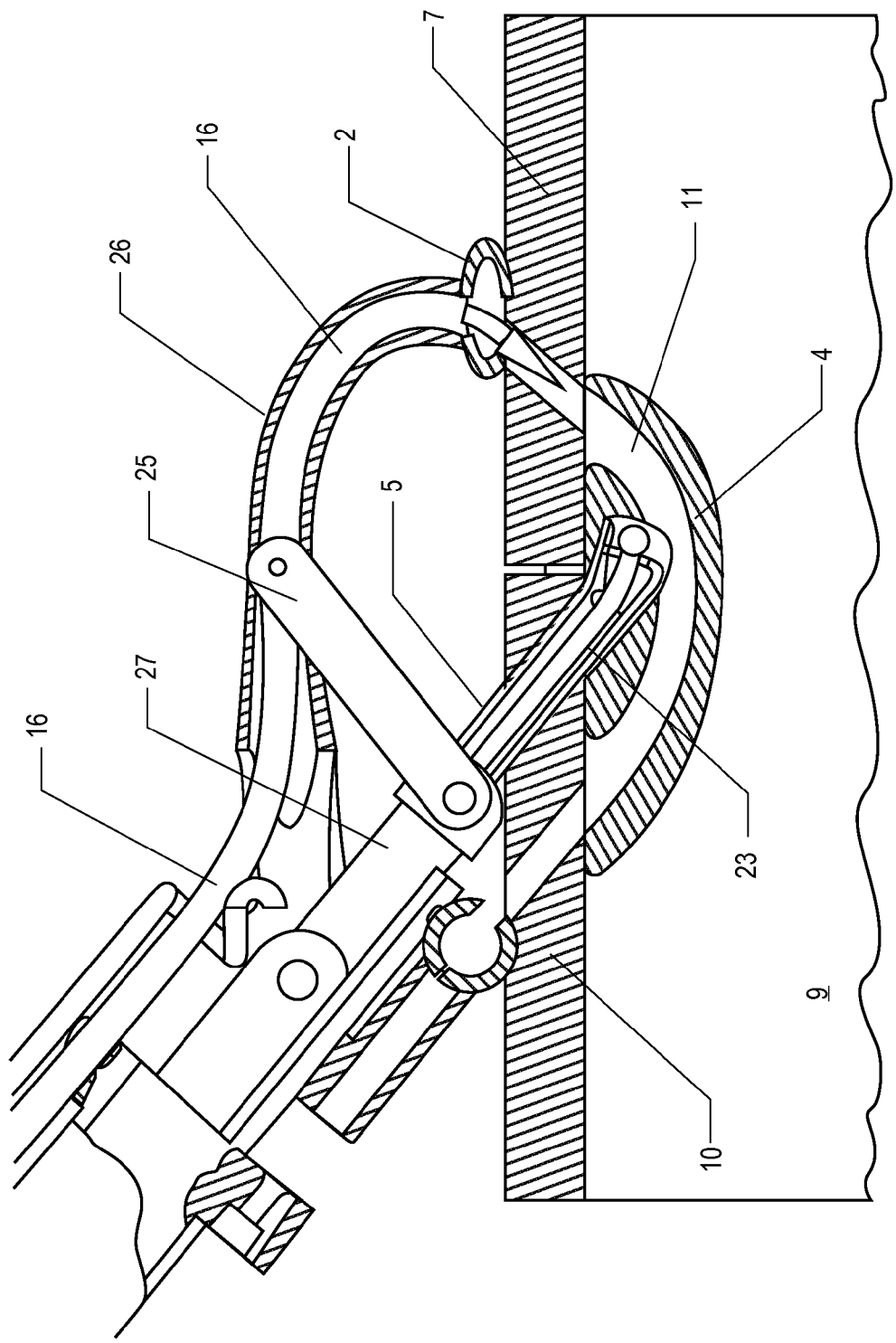

Once the needle-guide 26 is fully extended the needle-guide-link-actuator 27, needle-guide-link 25 and needle-guide 26 are all advanced forward down the intraarterial-foot-anchor 5 until the bolster 2 rests on the arterial surface. FIG. 19 illustrates repositioning of the extended needle-guide 26 to position the bolster 2 on the arterial surface. In this position the geometric relationship between the needle-guide exit and intraarterial-foot's channel opening 11 are in alignment. FIG. 20 illustrates alignment of the needle 16 with the intraarterial-foot channel 11, when the needle-guide is fully extended and advanced so that the bolster 2 is in contact with the arterial surface.

Figure 21:
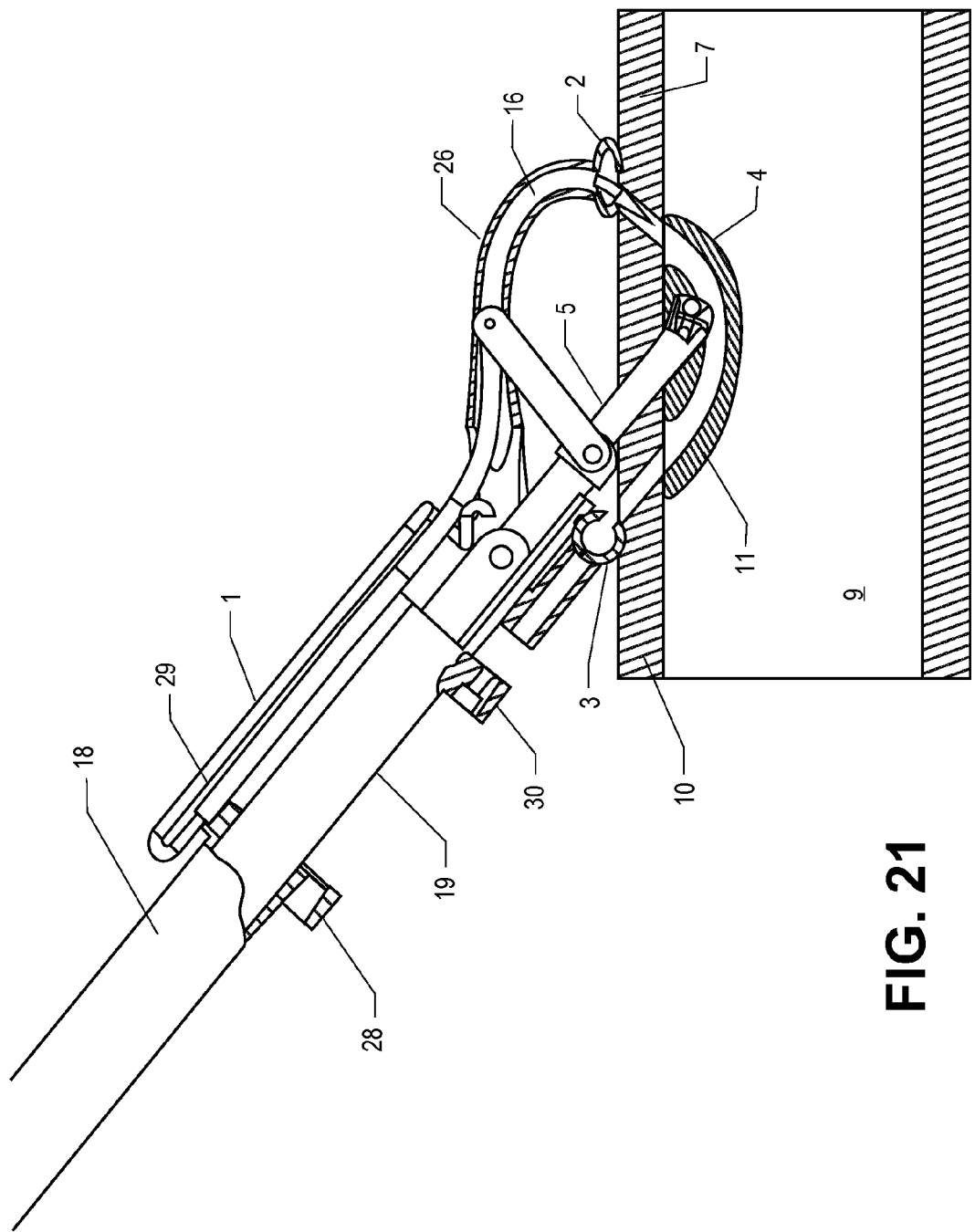
Figure 22:
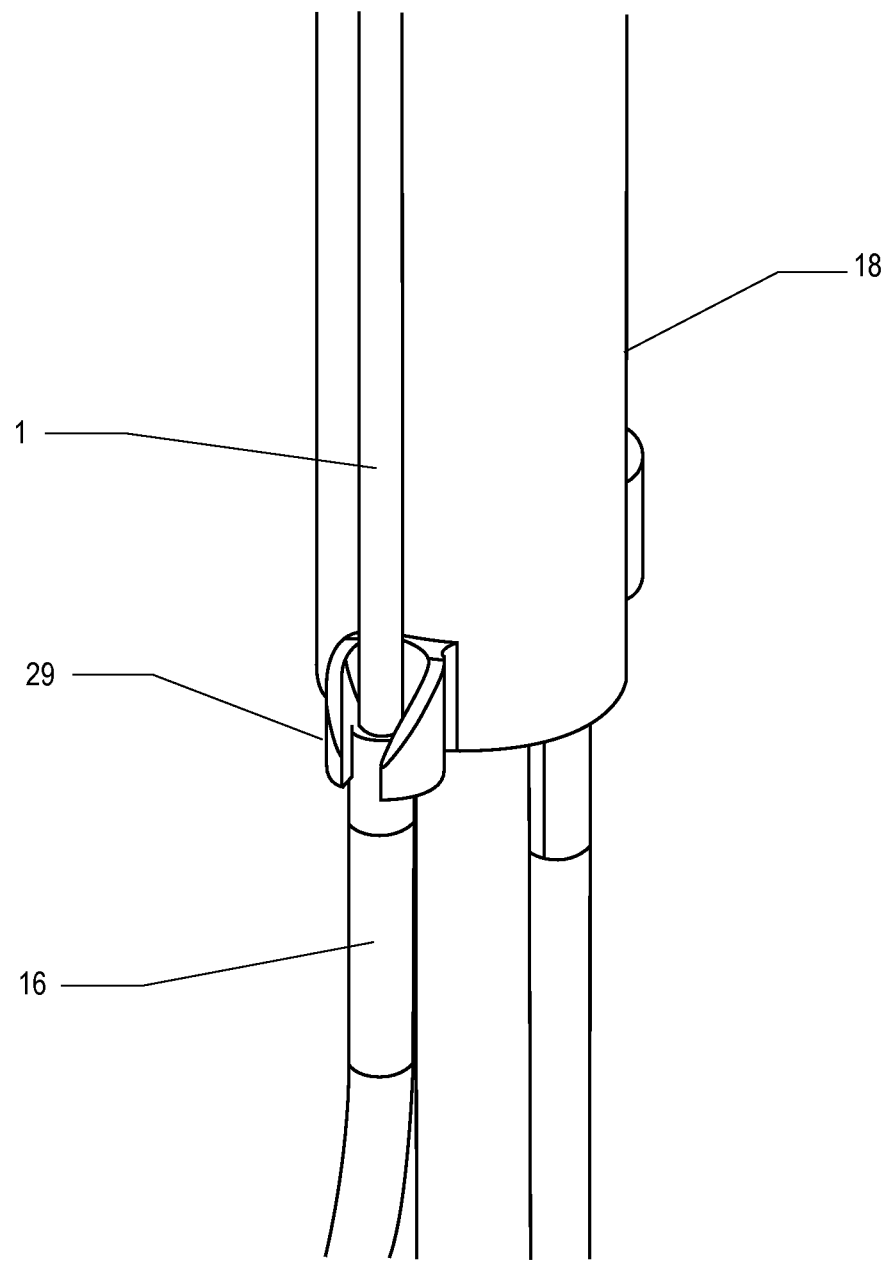
FIG. 22 is an isometric view of a proximal end of a closure element delivery component engaged with a driving mechanism of the interventional medical closure device according to the invention.

The flexible needle 16 is advanced by sliding the needle-driver and puller 18, concentrically about the intraarterial-foot-anchor 5, forward, towards the intraarterial-foot 4. FIG. 21 illustrates the needle-driver and pusher 18 in the start position and the direction of the needle-pusher and puller 18 and needle 16 movement. The needle-driver and puller 18 engages the proximal end of the needle 16 via a stepped shoulder 29. FIG. 22 illustrates the needle-pusher and puller's stepped shoulder 29 engaged with the proximal end of the needle 16. Note the opening to allow release of the suture 1. The stepped shoulder 29 has an opening to prevent the suture being captive and allows for the release of the suture 1 from the needle-driver and puller 18, once the needle 16 has been pushed fully forward, FIG. 23.

The advancing needle 16 penetrates the anterior wall of the artery 7, proximal to the arteriotomy, to locate the intraarterial-foot's channel 1. The intraarterial-foot's channel 11 guides the flexible needle 16 to the distal side of the arteriotomy, within the lumen 9. The needle 16 penetrates the anterior arterial wall 10 on the distal side of the arteriotomy to locate the bolster 3 and engage with the needle-gripper 19. FIG. 23 illustrates the path of the needle 16 penetrating the anterior wall proximal to the arteriotomy 7, through the intraarterial-foot's channel 11, through the anterior arterial wall distal to the arteriotomy 10 and engaging with the needle-gripper 19.

Figure 24:
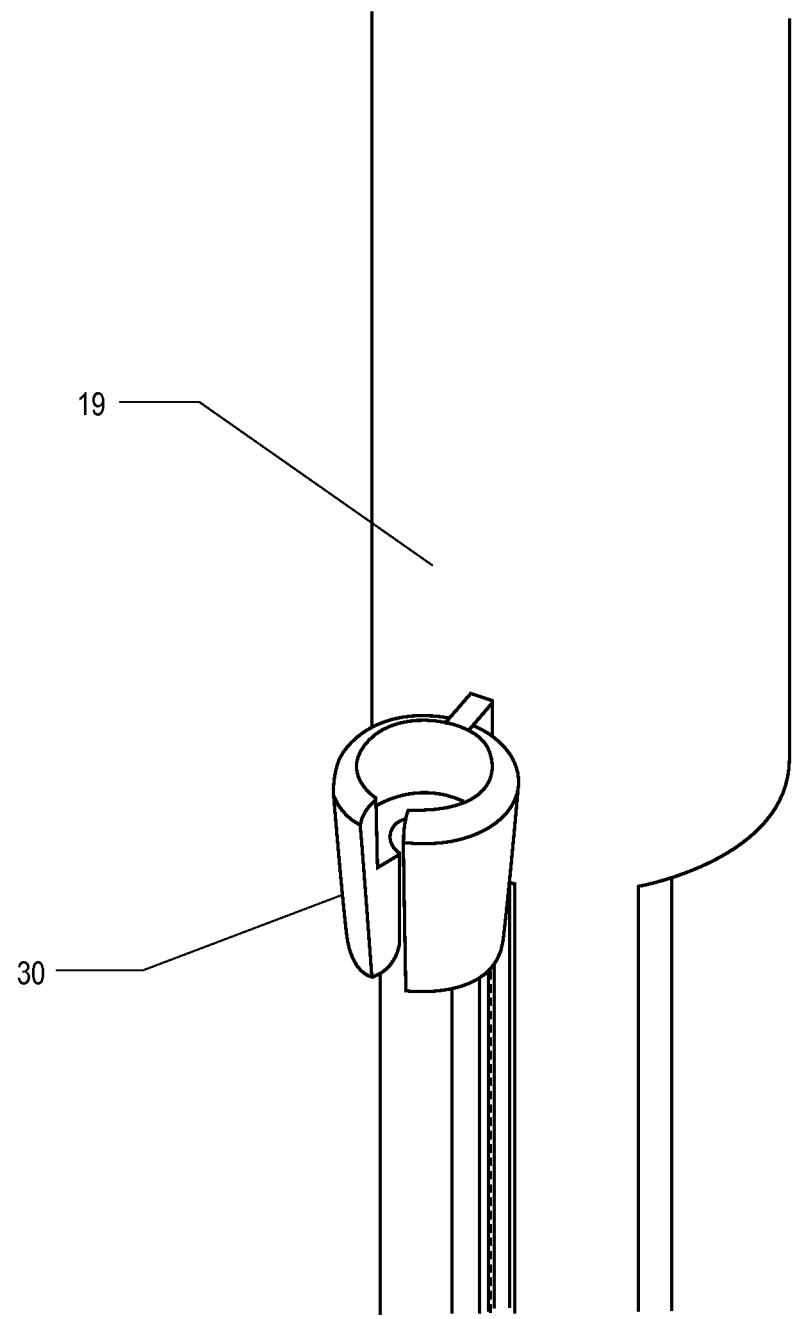
FIG. 24 is an isometric view of the closure element delivery component extraction mechanism of the interventional medical closure device according to the invention.
Figure 25:
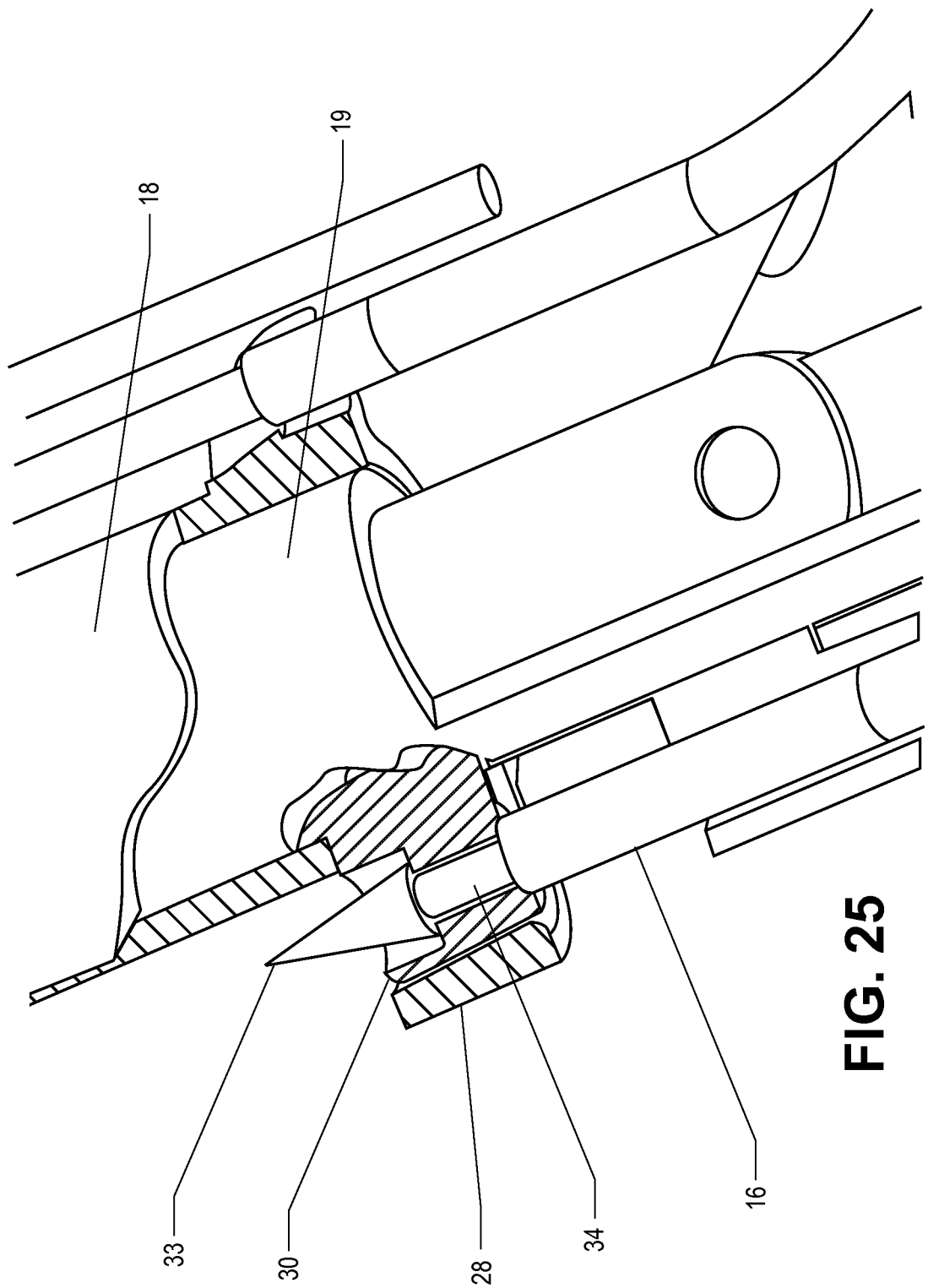
FIG. 25 is an isometric view of a distal end of the closure element delivery component of FIG. 22 engaged with the delivery component extraction mechanism of FIG. 24.

The needle 16 engages with the needle-gripper by penetrating a split annulus or collar 30. FIG. 24 illustrates the needle-gripper 19 and collar 30 showing its features. The collar 30 on the needle-gripper 19 expands as the needle tip or point 33 enters from its bottom edge, and contracts once the needle's recess 34 is aligned with the shoulder on the needle-gripper's collar 30 to passively clamp onto the recess proximal to the needle's tip. FIG. 25 illustrates the needle 16 engaged with the needle-griper's collar 30 and needle-pusher and puller's cone 28 engaged with the needle-gripper's collar 30.

Once the needle 16 is fully engaged with the needle-gripper as shown in FIG. 25, the needle-pusher and puller 18 moves axially away from the intraarterial-foot 4 so that the internal cone 28 of the needle-pusher and puller 18 mates with the external conical surface of the needle-gripper's collar 30. The mechanical interaction between the cone 28 of the needle-pusher and puller and conical surface of the needle-gripper's collar 30, cause the needle-gripper's collar 30 to actively clamp down on the needle recess 34.

Figure 26:
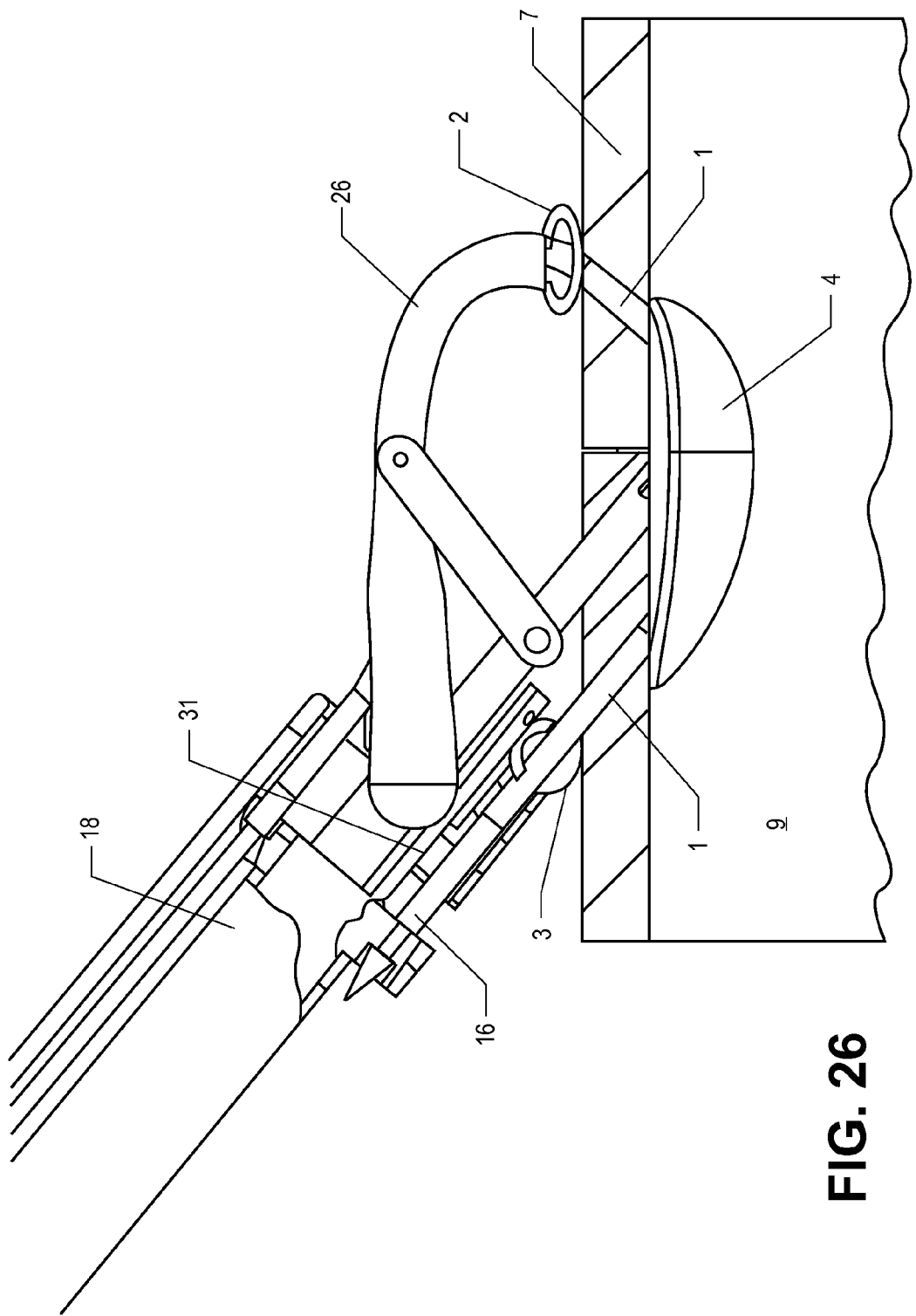
FIG. 26 is a cross-sectional, side view of the interventional medical closure device, in use.

The needle-pusher and puller 18 is moved axially along the intraarterial-foot-anchor 5 away from the intraarterial-foot 4 to pull the needle 16 out of the arterial wall, intraarterial-foot 4 and bolsters 2, 3, replacing it with the suture 1. FIG. 26 illustrates the needle 16 pulled from the arterial wall, intraarterial-foot 4 and bolsters 2, 3 to be replaced by the suture 1.

Figure 4:
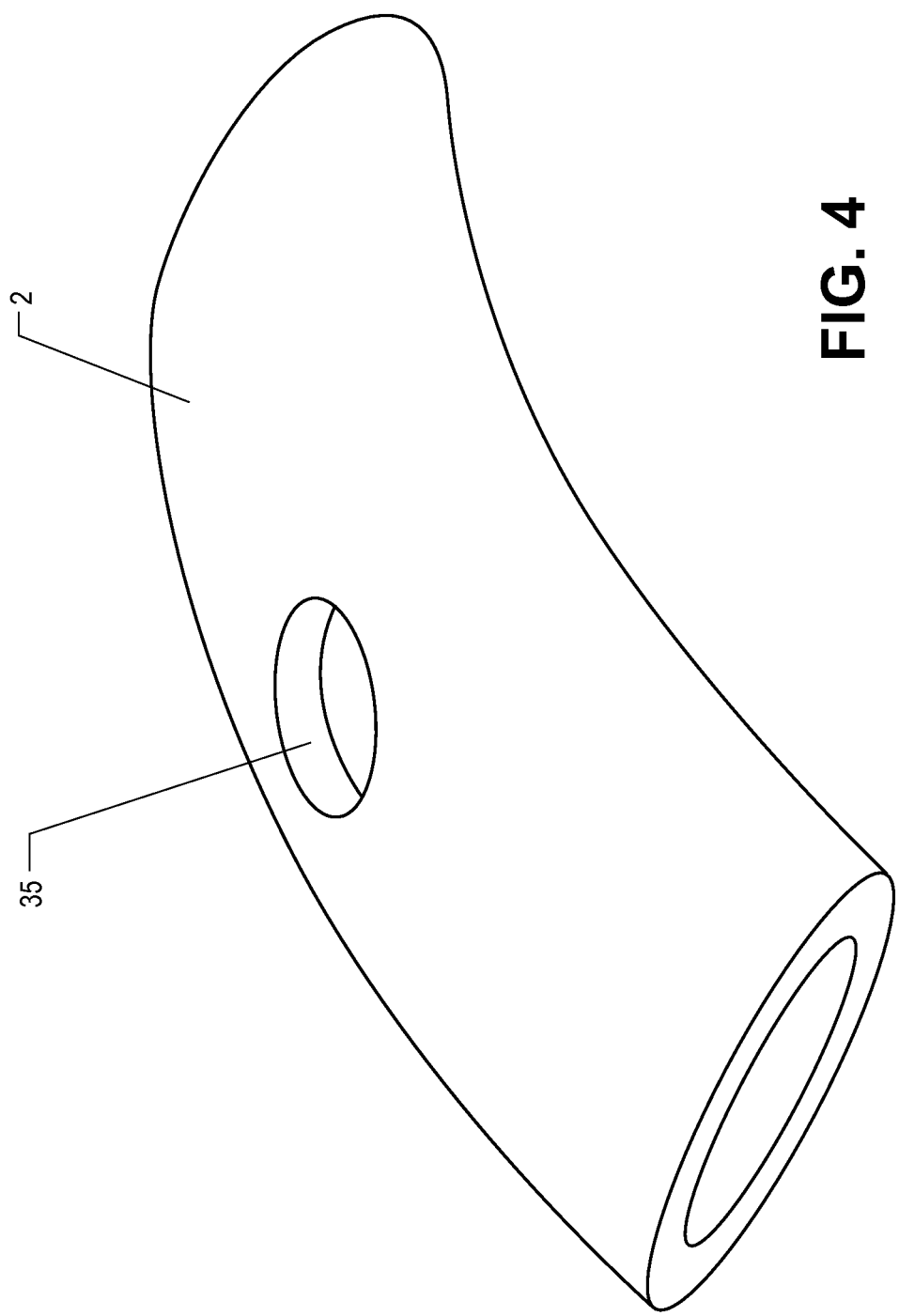
FIGS. 4 to 7 are isometric views of engagement elements of the interventional medical closure device according to the invention.
Figure 5:
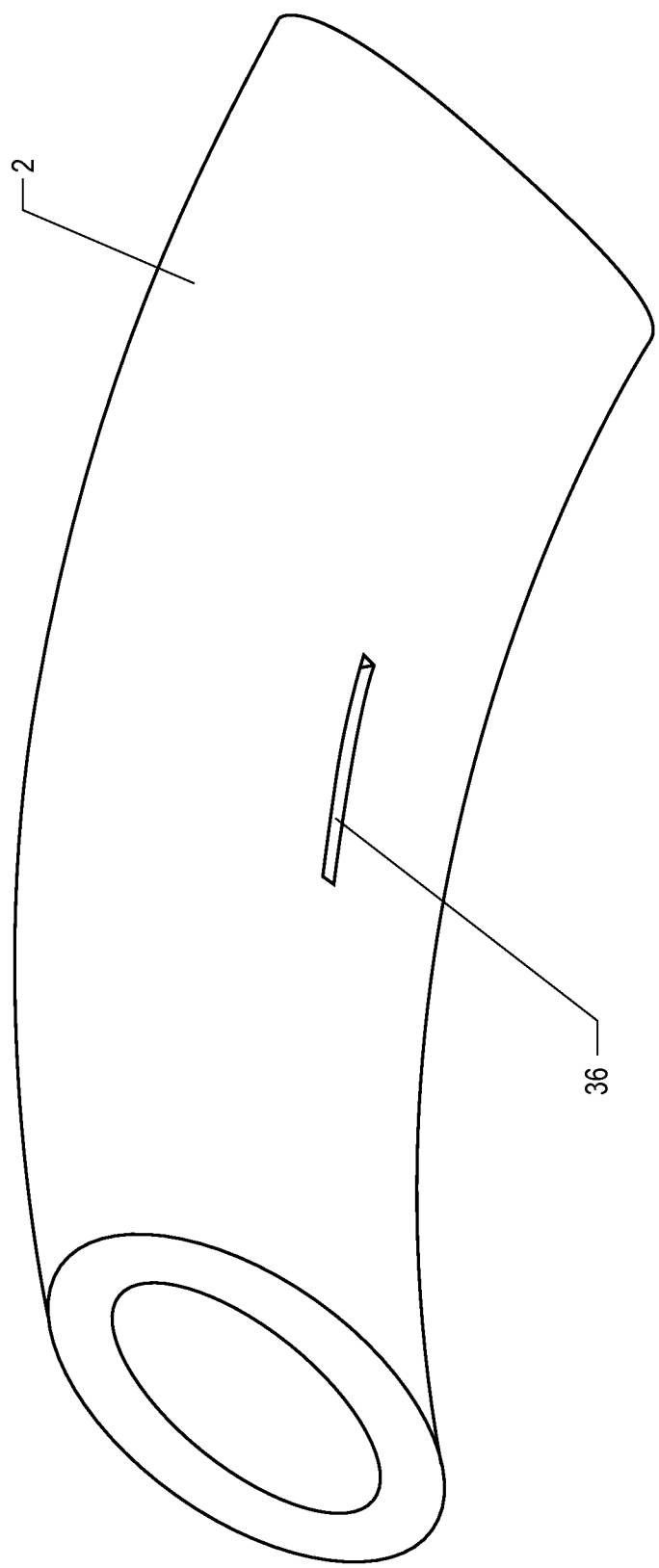
Figure 27:
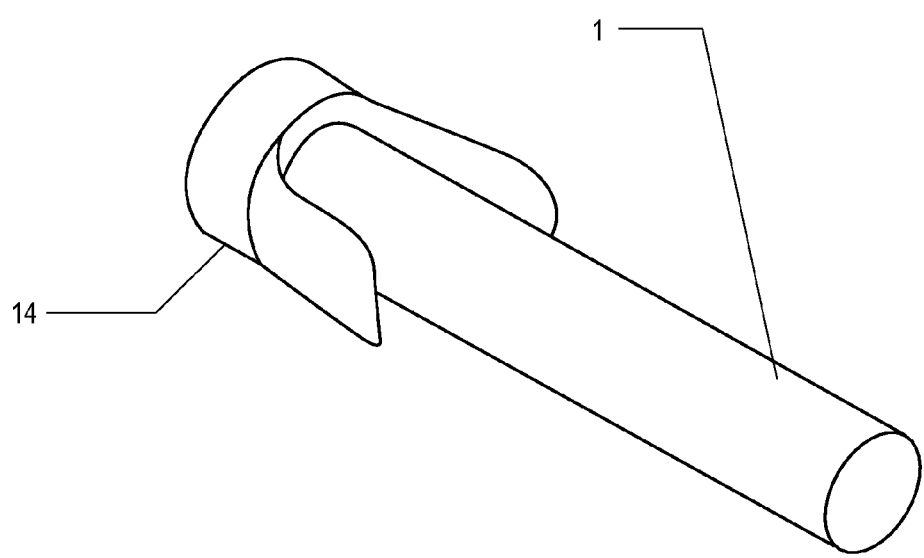
FIG. 27 is an isometric view of a proximal end of the closure element and closure element anchor of FIG. 21.

The suture 1 is prevented from passing all the way through the bolster 2 by operation of an attached suture-anchor 14 on its proximal end. FIG. 27 illustrates the suture-anchor 14 attached to the proximal end of the suture 1. The bolster 2 is designed with a cylindrical opening 35 in its anterior side and a thin slot opening 36 on its posterior side. FIGS. 4 and 5 illustrate the bolster 2 showing the anterior cylindrical opening 35 and the posterior thin slot opening 36. The cylindrical opening allows the needle 16 and suture 1 to enter the bolster 2 easily whilst the thin slot provides a clamping force on the exiting needle 16 and suture 1, by way of the elastomeric nature of the bolster material. The thin slot serves two functions, namely, to secure the bolster 2 in its initial pre-fire position relative to the distal end of the needle-guide 26, by clamping onto the needle recess 34, FIG. 20; and secondly, to prevent the suture anchor 14 from passing through the bolster 2. FIG. 28 illustrates the bolster 2 secured to the arterial surface by the suture 1 and the suture-anchor 14.

Figure 6:
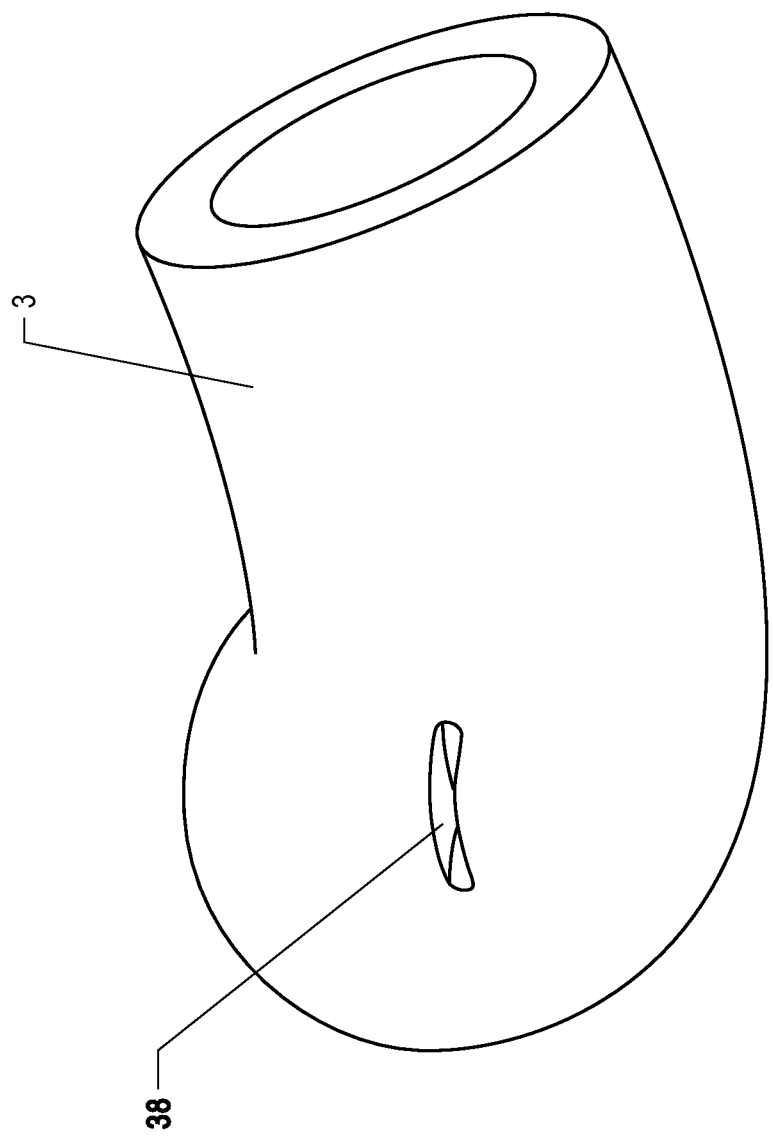
Figure 7:
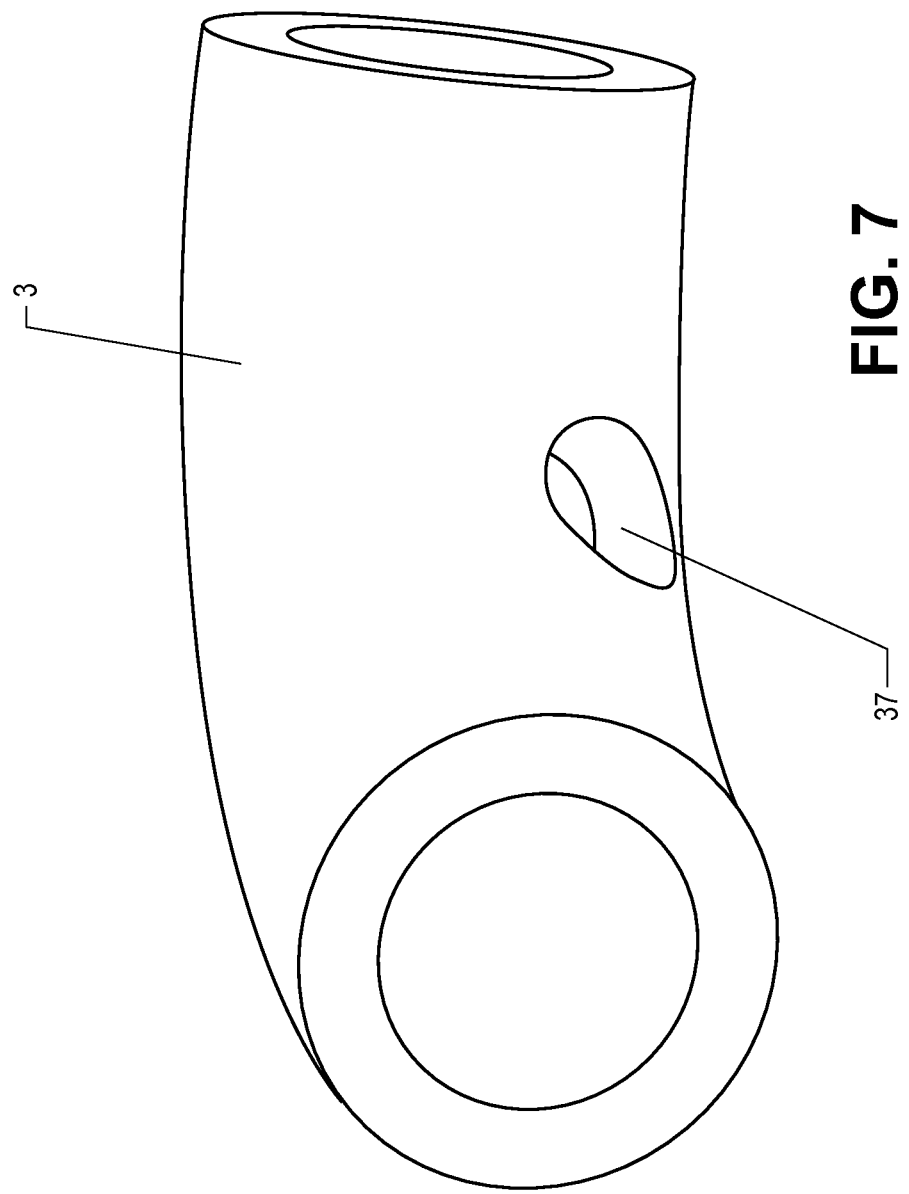

The bolster 3 is designed with a cylindrical opening 37 on it posterior surface and a thin slot opening 38 on its anterior surface, FIGS. 6 and 7. FIGS. 6 and 7 illustrate the bolster 3 showing the posterior cylindrical opening 37 and the anterior thin slot opening 38.

Figure 8:
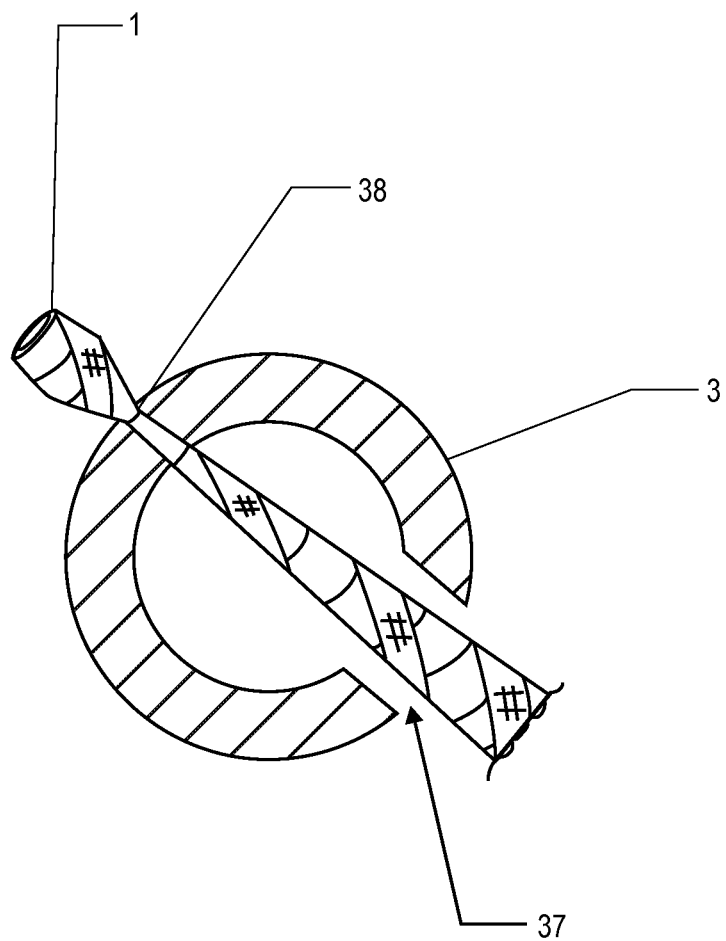
FIG. 8 is a cross-sectional, end view of an engagement element of the interventional medical closure device according to the invention.

The cylindrical opening on the posterior surface provides a large target for the needle point 33 to enter and allow easy passage of the needle 16 and suture 1. The thin slot opening on the anterior surface will allow passage of the needle 16 and suture 1 by everting the edges of the slot 38, in the direction of travel of the needle 16 and suture 1 away from the bolster 3. Relaxing of the everted slot edges when the suture travel stops will provide sufficient clamping force on the suture 1 to maintain any tension within the suture 1 and prevent the suture 1 from reversing direction relative to the bolster 3. A braided suture may further enhance this effect, in that under tension the braid is thinner, due to the fibres being more aligned under tension, than when the braid is relaxed. FIG. 8 illustrates the cross-section of the bolster 3 with the suture 1 in situ. Note, the pictorial representation of the narrow section of the suture 1 in tension compared to the thicker relaxed section of the suture 1. The thin slot edges provide a clamping effect on the suture 1 to maintain the tension.

Figure 29:
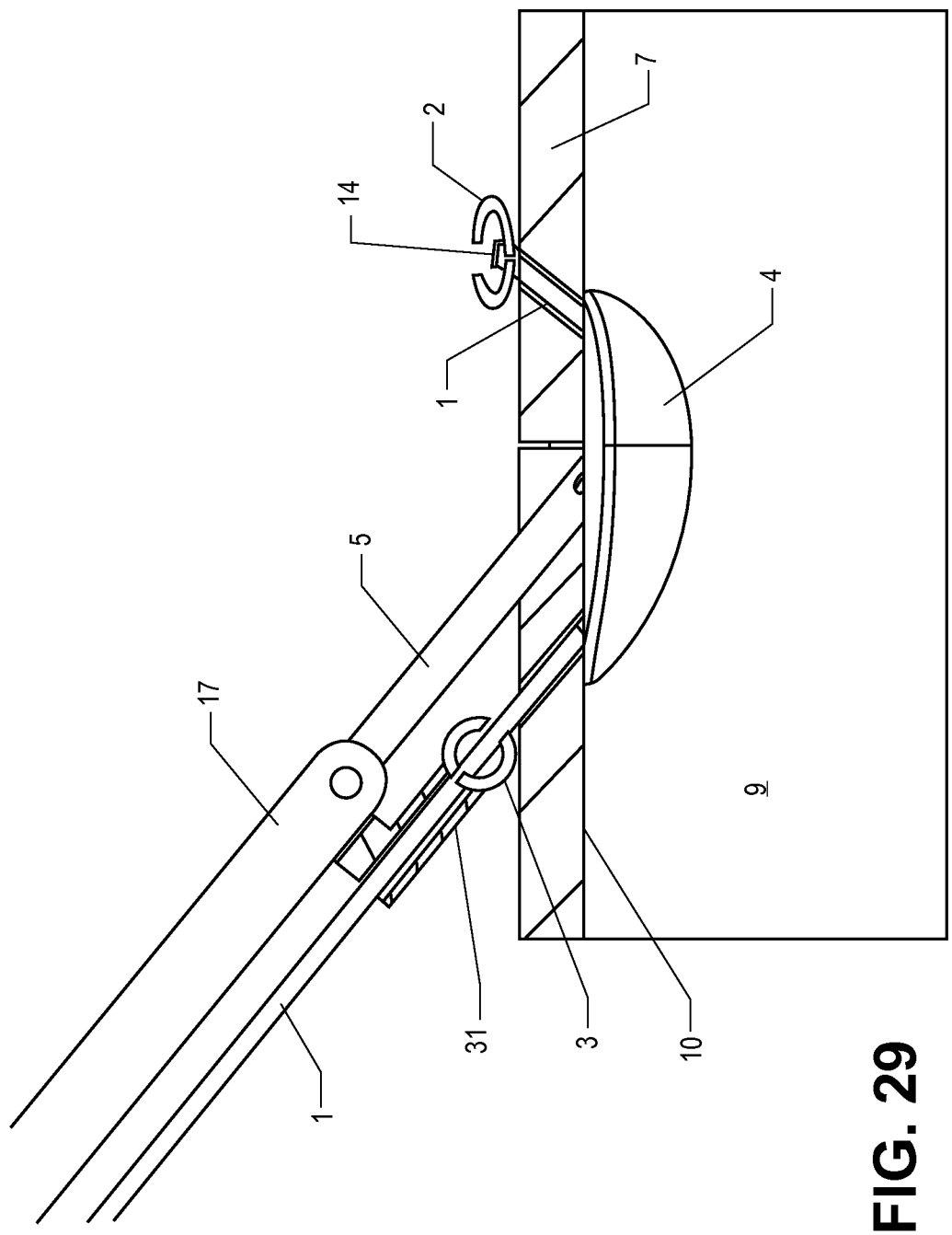
FIG. 29 is a cross-sectional, side view of the interventional medical closure device, in use.

The bolster 3 is maintained on the arterial surface by the bolster retainer 31 attached to the needle-guide-pivot and bolster-retainer 17, whilst the needle 16 and the suture 1 are pulled through the bolster 3. FIG. 29 illustrates the needle-guide-pivot and bolster-retainer 17 maintaining the position of the bolster 3 on the arterial surface and providing counter-tension for the needle 16 and suture 1 to be pulled through.

Once a pre-determined tension is achieved in the suture 1 between the bolster 2 and the bolster 3, the intraarterial-foot-anchor 5 is released from the intraarterial-foot 4. The intraarterial-foot 4 is secured to the intraarterial-foot-anchor 5 by operation of the wedge 13 on the distal tip of the intraarterial-foot-anchor 5, FIGS. 12, 14 and 15. FIGS. 14 and 15 illustrates the intraarterial-foot 4 and the intraarterial-foot-anchor 5 showing the wedge 13 interlock between them and wedge support member 15 that is maintaining the wedge 13. The wedge 13 configuration on the distal tip of the intraarterial-foot-anchor 5 is created and maintained by the wedge support member being positioned as shown in FIGS. 13, 14 and 15.

The wedge support member 15 is secured into position by engaging within the notch 39 either side of the intraarterial-foot-anchor's wedge section 13, FIGS. 13 and 15.

Release of the intraarterial-foot 4 from the intraarterial-foot-anchor 5 is achieved by applying sufficient tension to the foot-release-wire 23, which will collapse the wedge support member 15 to allow the wedge member 13 of the intraarterial-foot-anchor 5 to return to its cylindrical profile (by nature of the hyper-elastic material properties of the intraarterial-foot-anchor 5) to allow it to be removed from the intraarterial-foot's anchor-cavity 40. FIG. 30 illustrates the collapsed wedge support member 15, which in turn allows the return of the wedge member 13 to its original cylindrical profile for release of the intraarterial-foot-anchor 5 from the intraarterial-foot 4.

The suture tension between the bolster 2 and the bolster 3 effects an active closure of the arteriotomy 8. The bolsters 2, 3 distribute the suture tension on the adventitial surface of the artery parallel to the wound edges of the arteriotomy, with a resultant force bringing the wound edges of the arteriotomy into direct apposition, supported by the intraarterial-foot 4, to control and ensure proper alignment. FIG. 31 illustrates the final closure dynamics with respect to the distribution of the suture tension to effect an active closure of the arteriotomy. The intraarterial-foot 4 also distributes the suture tension's resultant force on the luminal surface of the artery. The luminal contact surface of the intraarterial-foot 4 may be porous to minimise the contact area with the luminal surface and allow nutrient exchange.

With reference to the arterial wall morphology, the fibrous adventitial layer is very tough and hence ideal to carry the distributed suture tension, while the intimal and endothelial layers are quite friable. Furthermore, as a consequence of the arterial wall's morphology, the arteriotomy 8 will often be of a circumferential nature perpendicular to the long axis of the artery, FIG. 31. The intraarterial-foot 4 prevents trauma or damage to the friable inner layer of the arterial wall by protecting these layers from direct contact with the suture 1, particularly from the sawing action of the braided suture during implantation, and distributes the suture's tension across the luminal surface. The bolsters 2, 3 distribute the suture's tension laterally across the arterial surface and parallel to the wound edges of the arteriotomy, ensuring an evenly distributed force along each wound edge of the arteriotomy to effect a secure closure. The configuration of the closure with the wound edges of the arteriotomy in direct apposition, with controlled alignment and absent of any transluminal impediments, ensures better wound healing. Advantageously, this direct apposition is a most expeditious form of healing.

The suture component of the closure system provides enhanced flexibility with respect to differing arterial wall thicknesses, other variations in anatomy and an amount of subsequent tension required to effect the closure.

All implantable components may be manufactured from an absorbable material such as polyglycolic acid which would, with time, be absorbed, leaving the artery and surrounding tissue to remodel to their original anatomical state, ensuring no long term sequale and allowing for re-stick or access at the same arterial site.

The foot element of the invention can be formed from a bioabsorbable material which allows the element to be absorbed over a period of time. Any suitable bioabsorbable material can be used. Typical bioabsorbable polymers that may be used include polylactide, polyglycolide, polydioxane, polycaprolactone and co-polymers thereof. The material selection will depend on desired absorption or degradation periods which will be a function of the time required for healing. Copolymers of polyglycolide and polylactide are available for example from Lakeshore Biomaterials. The engagement elements may be manufactured from the same types of materials.

The suture may be of monofilament or multifilament construction. A braided material is preferred as it is more robust, less susceptible to stress fractures. In addition a braided structure will swell and facilitate invasion by tissue with consequent increased security of locking within the bolster. The suture may, for example, be of braided polylactic acid material. One such suture is available, for example from B. Braun.

The invention is not limited to the embodiments hereinbefore described, with reference to the accompany drawings, which may be varied in construction and detail.

The invention claimed is:

1. An interventional medical implant for closing an opening in a tissue, the implant comprising:
a foot configured to engage only an internal surface of a vessel and connectable to a delivery element via an anchor cavity disposed within the foot, the foot having a convex upper engagement surface, a first opening on the convex upper engagement surface, a second opening on the convex upper engagement surface, and an anchor cavity opening on the convex upper engagement surface, wherein the first opening, the second opening, and the anchor cavity opening are configured to engage an internal surface of a vessel upon deployment of the foot and removal of the delivery element from the anchor cavity;
wherein the first opening, the second opening, and the anchor cavity opening each have a substantially circular cross section, each cross section having a center point,
wherein the center point of the first opening, the second opening, and the anchor cavity opening are aligned on a substantially straight line;

a closure element having a leading end and a proximal end, the closure element extending through the foot, whereby the leading end of the closure element extends out of the first opening on the convex upper engagement surface of the foot and the proximal end of the closure element extends out of the second opening on the convex upper engagement surface of the foot;

a first engagement element coupled to the leading end of the closure element; and a second engagement element coupled to the proximal end of the closure element, wherein the foot and the closure element are configured such that the leading end of the closure element is automatically guided from the second opening on the convex upper engagement surface to the first opening on the convex upper engagement surface when the leading end of the closure element is inserted and advanced through the first opening on the convex upper engagement surface.

2. An implant as claimed in claim 1 wherein the closure element extends through at least one of the engagement elements.

3. An implant as claimed in claim 1 wherein at least one of the engagement elements includes an engagement surface adapted for engagement with an external surface of a vessel.

4. An implant as claimed in claim 3 wherein the engagement surface is contoured to correspond to the external surface of the vessel.

5. An implant as claimed in claim 1 wherein at least one of the engagement elements comprises a bolster.

6. An implant as claimed in claim 1 wherein at least one of the engagement elements has an anterior side and a posterior side, the anterior side having an anterior opening therein, and the posterior side having a posterior opening therein.

7. An implant as claimed in claim 6 wherein the openings are of different dimensions.

8. An implant as claimed in claim 6 wherein one of the openings is generally circular and the other opening comprises a slot.

9. An implant as claimed in claim 6 wherein the first engagement element has a generally circular anterior opening and the posterior opening comprises a slot.

10. An implant as claimed in claim 6 wherein the second engagement element has a generally circular posterior opening and the anterior opening comprises a slot.

11. An implant as claimed in claim 1 wherein at least one of the engagement elements is flexible.

12. An implant as claimed in claim 1 wherein at least one of the engagement elements comprises a hollow body.

13. An implant as claimed in claim 1 wherein at least one of the engagement elements comprises a bioabsorbable material.

14. An implant as claimed in claim 1 wherein the engagement elements are configured to engage an external surface of an arterial wall.

15. An implant as claimed in claim 1 wherein the closure element comprises a suture member.

16. An implant as claimed in claim 15 further comprising a suture anchor for anchoring the suture to one of the engagement elements.

17. An implant as claimed in claim 15 wherein the suture comprises a braided material.

18. An implant as claimed in claim 15 wherein the suture comprises a bioabsorbable material.

19. An implant as claimed in claim 1 wherein the foot provides a tamponade.

20. An implant as claimed in claim 1 wherein the foot is movable between a delivery configuration and an engagement configuration.

21. An implant as claimed in claim 1 wherein the foot is engageable with an internal surface of a vessel to assist in closure of an opening through the vessel wall.

22. An implant as claimed in claim 21 wherein the foot comprises a profiled engagement surface for engagement with an internal surface of a vessel.

23. An implant as claimed in claim 1 wherein the foot has a substantially porous contact surface.

24. An implant as claimed in claim 1 wherein the foot comprises a guide for guiding the closure element.

25. An implant as claimed in claim 24 wherein the guide comprises a pathway for the closure element.

26. An implant as claimed in claim 25 wherein the pathway comprises a passageway extending from the first opening to the second opening through the guide.

27. An implant as claimed in claim 25 wherein the pathway comprises an open channel.

28. An implant as claimed in claim 1 wherein the foot comprises a bioabsorbable material.

29. An implant as claimed in claim 1 wherein the device comprises a delivery element to deliver the foot into an internal lumen of a vessel.

30. An implant as claimed in claim 29 wherein the foot is movable relative to the delivery element between an engagement configuration and a deployed configuration.

31. An implant as claimed in claim 30 wherein the delivery element comprises a holder element to hold the foot in the deployed configuration.

32. An implant as claimed in claim 29 further comprising a detachable guide, wherein the guide is detachable from the delivery element to deploy the foot in an internal lumen of a vessel.

33. An implant as claimed in claim 29 to wherein the device comprises a tubular element through which the delivery element and the foot may be delivered to a vessel.

34. An implant as claimed in claim 33 wherein the tubular element comprises an endovascular access sheath.

35. An implant as claimed in claim 34 wherein the sheath comprises a procedural sheath.

36. An implant as claimed in claim 1 wherein the device comprises a stabilizer element to stabilize the foot relative to a vessel.

37. An implant as claimed in claim 36 wherein the stabilizer element is engageable with an external surface of a vessel.

38. An implant as claimed in claim 36 wherein the stabilizer element is movable between a delivery configuration and an engagement configuration.

39. An interventional implant for closing an opening in a tissue, the implant comprising:
a foot configured to engage only an internal surface of a vessel and connectable to a delivery element via an anchor cavity disposed within the foot, the foot having a convex upper engagement surface, a first opening on the upper engagement surface, a second opening on the upper engagement surface, and an anchor cavity opening on the convex upper engagement surface, wherein the first opening, the second opening, and the anchor cavity opening are configured to engage an internal surface of a vessel upon deployment of the foot and removal of the delivery element from the anchor cavity;

wherein the first opening, the second opening, and the anchor cavity opening each have a substantially circular cross section, each cross section having a center point, wherein the center point of the first opening, the second opening, and the anchor cavity opening are aligned on a substantially straight line; and a closure element having a leading end and a proximal end, wherein the foot includes a passage between the first opening and the second opening configured to automatically guide the leading end of the closure element from the second opening on the upper engagement surface to the first opening on the upper engagement surface when the leading end of the closure element is inserted and advanced through the second opening on the upper engagement surface.

* * * * *